US007056715B1

(12) United States Patent
Andrews et al.

(10) Patent No.: US 7,056,715 B1
(45) Date of Patent: Jun. 6, 2006

(54) GST SEQUENCES FROM SOYBEAN AND THEIR USE IN THE PRODUCTION OF HERBICIDE RESISTANT PLANTS

(75) Inventors: John Christopher Andrews, Bracknell (GB); Ian Cummins, Durham (GB); Robert Edwards, Durham (GB); Ian Jepson, Bracknell (GB); Mark Skipsey, Durham (GB); Karen Jane Townson, Bracknell (GB)

(73) Assignee: Syngenta Limited, Guildford Surrey (GB)

( * ) Notice: Subject to any disclaimer, the term of this patent is extended or adjusted under 35 U.S.C. 154(b) by 388 days.

(21) Appl. No.: 10/088,945

(22) PCT Filed: Sep. 18, 2000

(86) PCT No.: PCT/GB00/03573

§ 371 (c)(1),
(2), (4) Date: Sep. 24, 2002

(87) PCT Pub. No.: WO01/21770

PCT Pub. Date: Mar. 29, 2001

(30) Foreign Application Priority Data

Sep. 21, 1999 (GB) ................................. 9922346.3

(51) Int. Cl.
*C12N 9/10* (2006.01)

(52) U.S. Cl. ...................................... 435/193; 536/23.2
(58) Field of Classification Search ................ 435/193; 536/23.2
See application file for complete search history.

(56) References Cited

U.S. PATENT DOCUMENTS 6,063,570 A    5/2000    McGonigle ..................... 435/6

FOREIGN PATENT DOCUMENTS

| WO | WO 99 14337 | 3/1999 | ..................... 15/54 |
| WO | WO 00 18936 | 4/2000 | ..................... 15/82 |
| WO | WO 00 47728 | 8/2000 | ....................... 9/10 |

OTHER PUBLICATIONS

Shiota et al Herbicide-resistant tobacco plants expressing the fused enzyme between rat cytochrome P4501A1 (CYP1A1) and yeast NADPH-cytochrome P450 oxidoreductase. Plant Physiol. Sep. 1994;106(1):17-23.*
A.M. Gulick et al. "Forced Evolution of Glutathione S-Transferase To Create a More Efficient Drug Detoxification Enzyme", Pro Natl. Acad. Sci. 92: 8140-8144. (Aug. 1995).*
Andrews et al., *Glutathione Transferase Activities toward Herbicides Used Selectively in Soybean Pesticide Science*, vol. 51 (1997), pp. 213-222.

Andrews et al., *Glutathione transferases in soybean Journal of Experimental Botany*, vol. 49, Supplemental (May 1998), pp. 22-23.
Blewitt, M., *BNLGHi10422 Six-day Cotton fiber Gossypium hirsutum cDNA 5' similar to (AF064201) glutathione S-transferase* [*Gossypium hirsutum*], mRNA sequence Accession No.: A1731664 [database, EMBL online], (Jun. 1999).
Federspiel et al., *Arabidopsis thaliana chromosome I BAC F23H11 genomic sequence, complete sequence* Accession No.: AC007258 [database, EMBL online], (Apr. 1999).
Frendo et al., *Localisation of glutathione and homoglutathione in Medicago truncatula is correlated to a differential expression of genes involved in their synthesis The Plant Journal*, vol. 17(2) (1999), pp. 215-219.
Frendo et al., *Medicago truncatula putative glutathione synthetase (GSHS1) mRNA, partial cds.* Accession No.: AF075699 [database, EMBL online], (May 1999).
Frendo et al., *Medicago truncatula putative glutathione synthetase (GSHS2) mRNA, partial cds.* Accession No.: AF075700 [database, Genbank online], (Aug. 2001).
Klapheck et al., *Properties and localization of the homoglutathione synthetase from phaseolus-coccineus leaves Physiologia Plantarum*, vol. 74, No. 4 (1988), pp. 733-739.
Kovari, I.A., and Goldsbrough, P.B., *Lycopersicon esculentum glutathione synthetase (GSH2) mRNA, complete cds.* Accession No.: AF017984 [database, EMBL online], (Sep. 1997).
Matamoros et al., *Glutathione and Homoglutathione Synthesis in Legume Root Nodules Plant Physiology*, vol. 121 (Nov. 1999), pp. 879-888.
McGonigle et al., *A Genomics Approach to the Comprehensive Analysis of the Glutathione S-Transferase Gene Family in Soybean and Maize Plant Physiology*, vol. 124 (Nov. 2000), pp. 1105-1120.
McGonigle et al., *Homoglutathione Selectivity by Soybean Glutathione S-Transferases Pesticide Biochemistry and Physiology*, vol. 62 (1998), pp. 15-25.
McKersie et al., *Superoxide dismutase enhances tolerance of freezing stress in transgenic alfalfa (Medicago sativa L.) Plant Physiology*, vol. 103, No. 4 (Dec. 1993) pp. 1155-1163.
Riechers et al., *Aegilops tauschii glutathione S-transferase TSI-1 mRNA, complete cds.* Accession No.: AF004358 [database, EMBL online], (Jun. 1997).

(Continued)

Primary Examiner—Rebecca Prouty
(74) *Attorney, Agent, or Firm*—Syngenta Limited

(57) ABSTRACT

The present invention relates to inter alia, Glutathione-S-Transferase (GST) and homoglutathione synthetase sequences from soybean and their use in the production of plants which are resitant to herbicides which comprise fomesafen and/or acifluorfen. In a particular embodiment the invention provides a GST depicted as SEQ ID No. 10 and a homoglutathione synthetase depicted as SEQ ID No. 1.

3 Claims, 4 Drawing Sheets

OTHER PUBLICATIONS

Schaefer et al., *B. juncea mRNA for glutathione synthetase* Accession No.: Y10984.1 [database, EMBL online], (Jul. 1997).

Shoemaker et al., *sa63f01.y1 Gm-c1004 Glycine max cDNA clone Genome Systems Clone ID: Gm-C1004-3986 5' similar to TR:004562 004562 T7N9.15;, mRNA sequence* Accession No.: AI440996 [database, EMBL online], (Mar. 1999).

Shoemaker et al., *sil4cll.y1 Gm-c1029 Glycine max cDNA clone Genome Systems Clone ID: Gm-c1029-1197 5' similar to TR: 004941 004941 Glutathione S-Transferase TSI-1;, mRNA sequence* Accession No.: AW471665 [database, Genbank online], (Feb. 2000).

Skipsey et al., "Purification and characterization of glutathione transferase enzymes from soybean seedlings," in *British Crop Protection Conference—Weeds* (British Crop Protection Council, 1997), pp. 789-794.

Skipsey et al., *Substrate and thiol specificity of a stress-inducible glutathione transferase from soybean Federation of European Biochemical Societies Letters*, vol. 409 (1997) pp. 370-374.

Skipsey, M., *Glycine max mRNA for homoglutathione synthetase (hGS gene)* Accession No.: AJ272035 [database, EMBL online], (May 2000).

* cited by examiner

GST SEQUENCES FROM SOYBEAN AND THEIR USE IN THE PRODUCTION OF HERBICIDE RESISTANT PLANTS

This application is a 371 of International Application No. PCT/GB00/03573, filed Sep. 18, 2000, which is incorporated herein by reference, and which claims priority from GB9922346.3, filed Sep. 21, 1999.

The present invention relates inter alia, to Glutathione-S-transferase (GST) sequences and their use in methods for the production of herbicide resistant plants. In particular the polynucleotides according to the invention may be used in methods for the production of plants which are resistant to herbicides comprising fomesafen and/or acifluorfen.

Plants which are substantially "tolerant" to a herbicide when they are subjected to it provide a dose/response curve which is shifted to the right when compared with that provided by similarly subjected non tolerant like plants. Such dose/response curves have "dose" plotted on the x-axis and "percentage kill", "herbicidal effect" etc. plotted on the y-axis. Tolerant plants will typically require at least twice as much herbicide as non tolerant like plants in order to produce a given herbicidal effect. Plants which are substantially "resistant" to the herbicide exhibit few, if any, necrotic, lytic, chlorotic or other lesions when subjected to the herbicide at concentrations and rates which are typically employed by the agrochemical community to kill weeds in the field. Hereinafter the words (i) "tolerant" and (ii) "resistant" when used individually mean "tolerant and/or resistant".

Herbicide resistant plants are already available within the art for example, ROUNDUP READY™ Soya which is resistant to herbicides having as a site of action the enzyme 5-enolpyruvylshikimate-3-phosphate synthase, such as those agrochemicals containing glyphosate. One of the advantages of these plants is that the farmer can apply the herbicides to fields containing the resistant crop plants and weeds using "over-the-top application", to kill the weeds.

Other examples of products for use in methods for the production of herbicide resistant plants are provided in International Patent Application Publication Number WO 93/01294 and WO99/14337. Here the resistance is achieved by inserting into the plant a polynucleotide which provides for the production of a glutathione-S-transferase (GST) enzyme which is involved with the detoxification of the herbicide. Glutathione-S-transferase enzymes have been shown to exist in various organisms such as bacteria, fungi, yeast, plants, mammals and fish and may exist as homo or heterodimers with subunits typically between 24 and 30 KDa. It has been shown that herbicide detoxification is achieved by the conjugation of the herbicide with the free thiol glutathione (GSH), a tripeptide (gamma-glutamyl-cysteinyl-glycine) within the plant (Cole D. J. 1994 Pesticide Science. 42 pp209–222). Such conjugation is catalysed by GST. Detoxification of herbicides has also been shown to occur following the conjugation of the herbicide with homoglutathione, which is the predominant thiol in some leguminous species. Homoglutathione (hGSH) is also a tripeptide (gamma-glutamyl-cysteinyl-Beta-alanine) but differs from GSH by the addition of Beta-alanine instead of a glycine to the gamma-glutamyl-cysteinyl part.

Thus, the present invention seeks to provide inter alia, novel polynucleotides which encode proteins which can be used in methods of providing plants with high levels of resistance to a herbicide which comprises fomesafen and/or acifluorfen.

According to the present invention there is provided a Glutathione-S-transferase (GST) comprising the amino acid sequence depicted as SEQ ID No. 10 or a variant GST having at least 80% identity therewith with the proviso that said variant GST does not comprise the amino acid sequence depicted as SEQ ID No. 36. (which corresponds to the sequence of clone SE3.03B09 listed as SEQ ID No. 8 in International Patent Application Publication Number WO00/18936). In a further embodiment of the present invention said variant OST has at least 85% identity to the sequence depicted as SEQ ID No. 10. In a still further embodiment of the present invention said variant GST has at least 90% identity to the sequence depicted as SEQ ID No. 10. In a still further embodiment of the present invention said variant GST has at least 91% identity to the sequence depicted as SEQ ID No. 10. In a still further embodiment of the present invention said variant GST has at least 92% identity to the sequence depicted as SEQ ID No. 10. In a still further embodiment of the present invention said variant OST has at least 93% identity to the sequence depicted as SEQ ID No. 10. In a still further embodiment of the present invention said variant GST has at least 94% identity to the sequence depicted as SEQ ID No. 10. In a still further embodiment of the present invention said variant GST has at least 95% identity to the sequence depicted as SEQ ID No. 10. In a still further embodiment of the present invention said variant GST has at least 96% identity to the sequence depicted as SEQ ID No. 10. In a still further embodiment of the present invention said variant GST has at least 97% identity to the sequence depicted as SEQ ID No. 10. In a still further embodiment of the present invention said variant GST has at least 98% identity to the sequence depicted as SEQ ID No. 10. In a still further embodiment of the present invention said variant GST has at least 99% identity to the sequence depicted as SEQ ID No. 10. The present invention still further provides a GST comprising the sequence depicted as SEQ ID No. 7, 8 or 9 or a GST variant having at least 80% identity therewith with the proviso that said variant does not encode the sequence depicted as SEQ ID No. 37 (which corresponds to the sequence of clone SS1.PK0014.A1 listed as SEQ ID No. 22 in International Patent Application Publication Number WO00/18936). The percentage of sequence identity for proteins is determined by comparing two optimally aligned sequences over a comparison window, wherein the portion of the amino acid sequence in the comparison window may comprise additions or deletions (i.e. gaps) as compared to the initial reference sequence (which does not comprise additions or deletions) for optimal alignment of the two sequences. The percentage is calculated by determining the number of positions at which the identical amino acid residue occurs in both sequences to yield the number of match positions, dividing the number of match positions by the total number of positions in the window of comparison and multiplying the result by 100 to yield the percentage of sequence identity. When calculating the percentage sequence identity the sequences may be aligned allowing for up to 3 gaps with the proviso that in respect of the gaps, a total of not more than 15 amino acid residues is affected. Optimal alignment of sequences for comparison may also be conducted by computerised implementations of known algorithms. In a particular embodiment of the present invention the sequence identity is calculated using the FASTA version 3 algorithm which uses the method of Pearson and Lipman (Lipman, D. J. and Pearson, W. R. (1985) Rapid and Sensitive Protein Similarity Searches and Science. 227:1435–1441 and Pearson, W. R. and Lipman, D. J. (1988) Improved tools for biological sequence comparison. PNAS. 85:2444–2448) to search for similarities between the reference sequence (also termed the query sequence) and any group of sequences (termed further sequences). Methods also exist in the art which enable the percentage sequence identity between polynucleotide sequences to be calculated.

The protein may differ from the basic GST protein sequence (such as SEQ ID No. 10) by conservative or non-conservative amino acid substitutions. A conservative substitution is to be understood to mean that the amino acid is replaced with an amino acid with broadly similar chemical properties. In particular conservative substitutions may be made between amino acids within the following groups:

(i) Alanine and Glycine;
(ii) Serine and Threonine;
(ii) Glutamic acid and Aspartic acid;
(iii) Arginine and Lysine;
(iv) Asparagine and Glutamine;
(v) Isoleucine and Leucine,
(vi) Valine and Methionine;
(vii) Phenylalanine and Tryptophan.

In general, more conservative than non-conservative substitutions will be possible without destroying the GST properties of the proteins. Suitable variant proteins in accordance with the present invention may be determined by testing the GST properties of the protein using routine methods which are well known to the person skilled in the art. Such variant proteins may also be synthesised chemically using standard techniques.

The present invention further provides a GST or variant as described above wherein said GST or variant is capable of conferring resistance and/or tolerance to a herbicide which comprises fomesafen and/or acifluorfen. The herbicide may also comprise other Diphenyl ethers or Sulphonylureas such as Chlorimuron Ethyl and/or Chloroacetanilides such as acetochlor.

The present invention still further provides a polynucleotide comprising a region which encodes a GST or a variant GST as described above. In a particular embodiment of the present invention said polynucleotide comprises the sequence depicted as SEQ ID No. 14.

The present invention still further provides a polynucleotide sequence which is the complement of one which binds to a polynucleotide as described above at a temperature of between 60° C. and 65° C. in 0.3 strength citrate buffered saline containing 0.1% SDS followed by rinsing at the same temperature with 0.3 strength citrate buffered saline containing 0.1% SDS wherein said polynucleotide sequence still encodes a functional GST with the proviso that said polynucleotide sequence is not the sequence depicted as SEQ ID No. 38. This sequence corresponds to the sequence of clone SE3.03B09 listed as SEQ ID No. 7 in International Patent Application Publication Number WO00/18936. The aforementioned hybridisation conditions are well known to the person skilled in the art as high stringency conditions. As an alternative to the protocol mentioned above the skilled person may identify a polynucleotide sequence encoding a GST variant according to the present invention under the following conditions: hybridisation at a temperature of about 65° C. in a solution containing 6×SSC, 0.01% SDS and 0.25% skimmed milk powder, followed by rinsing at the same temperature in a solution containing 0.2×SSC and 0.1% SDS.

The present invention still further provides a polynucleotide sequence as described above which is not a sequence selected from the group of sequences listed under accession numbers: AF004358; AC000348; AF051214; AF051238 and P32110.

The present invention still further provides a polynucleotide comprising the sequence depicted as SEQ ID No. 11, 12 or 13 or a polynucleotide sequence which is the complement of one which hybridises to any one of SEQ ID Nos. 11, 12 or 13 under stringent conditions with the proviso that said polynucleotide sequence is not a sequence selected from the group depicted as SEQ ID Nos. 39 to 43. These sequences correspond to the sequence of clones SS1.PK0014.A1; SES8W.PK0028.C6; SR1.PK0011.D6; SS1.PK0020.B10; SSM.PK0067.G5 listed as SEQ ID Nos. 21, 13, 15, 23 and 25 respectively in International Patent Application Publication Number WO00/18936.

The present invention further provides a polynucleotide sequence as described in the preceding paragraph wherein said polynucleotide sequence or the amino acid sequence which it encodes, is not a sequence selected from the group of sequences listed under accession number; P32110, U20809, Q03663, P32111, P46421, AJ000923, AF004358, AC000348, AF051214 or AF051238. These accession numbers relate to GST and putative GST sequences in the database (and also depicted in the sequence listing) which exhibit a low % identity to the sequences according to the present invention.

In a further aspect of the present invention there is provided a protein comprising the amino acid sequence depicted as SEQ ID No. 1 or a protein variant having at least about 70% identity therewith wherein the said protein or variant is capable of catalysing the addition of Beta-alanine onto gamma glutamylcysteine. In a further embodiment of the present invention said protein variant has at least 75% identity with the sequence depicted as SEQ ID No. 1. In a still further embodiment of the present invention said protein variant has at least 80% identity with the sequence depicted as SEQ ID No. 1. In a still further embodiment of the present invention said protein variant has at least 85% identity with the sequence depicted as SEQ ID No. 1. In a still further embodiment of the present invention said protein variant has at least 90% identity with the sequence depicted as SEQ ID No. 1. In a still further embodiment of the present invention said protein variant has at least 95% identity with the sequence depicted as SEQ ID No. 1. In a still further embodiment of the present invention said protein variant has at least 96% identity with the sequence depicted as SEQ ID No. 1. In a still further embodiment of the present invention said protein variant has at least 97% identity with the sequence depicted as SEQ ID No. 1. In a still further embodiment of the present invention said protein variant has at least 98% identity with the sequence depicted as SEQ ID No. 1. In a still further embodiment of the present invention said protein variant has at least 99% identity with the sequence depicted as SEQ ID No. 1. The sequence identity may be calculated and the protein variants created/identified in a manner analogous to that described above.

The present invention still further provides a protein variant as described in the preceding paragraph having a Km for Beta-alanine which is less than the said variants Km for glycine when calculated using the same method. In a further embodiment of the present invention said protein variant has a Km for Beta-alanine which is less than or equal to about 1 mM and a Km for glycine which is higher than 1 mM when calculated using the same method. In a still further embodiment of the present invention said protein variant has a Km for Beta-alanine which is less than or equal to about 0.8 mM and a Km for glycine which is higher than 0.8 mM when calculated using the same method. The Km or "Michaelis-Menten Constant" is a kinetic parameter which indicates the substrate concentration at which the initial velocity of the reaction ($V_0$) is half maximal. Methods for the calculation of Km are well known to the person skilled in the art.

The present invention further provides a protein variant as described above which has a Vmax for Beta-alanine which is greater than the said variants Vmax for glycine when calculated using the same method. Vmax is also know the skilled person as the maximum rate of enzyme reaction i.e. the point at which the enzyme becomes saturated with substrate.

The present invention further provides a protein variant as described above comprises a sequence which contains at least one of the amino acid sequence regions depicted in the group depicted as SEQ ID No. 2 (KKIQQELAKP); SEQ ID No. 3 (CFAGLWSL); SEQ ID No. 4 (VMKPQREGGGN-NIYG) and SEQ ID No. 5 (AAYILMQRIFP). In a still further embodiment of the present invention said protein variant comprises a sequence which contains at least two amino acid sequence regions selected from the group depicted as SEQ ID No. 2, 3, 4 or 5. In a still further embodiment of the present invention said protein variant comprises a sequence which contains all of the amino acid sequence regions depicted as SEQ ID No. 2, 3, 4 or 5.

The present invention still further provides a polynucleotide comprising a region encoding the protein or protein variant as described above. In a further embodiment of the present invention said polynucleotide comprises the sequence depicted as SEQ ID No. 6.

The present invention still further provides a polynucleotide sequence which is the complement of one which hybridises to the polynucleotide depicted as SEQ ID No. 6 under stringent conditions wherein said polynucleotide sequence still encodes a protein which is capable of catalysing the addition of Beta-alanine onto gamma glutamyl-cysteine. Such hybridisation conditions are described above.

The present invention still further provides a polynucleotide comprising a first region comprising a polynucleotide encoding a GST or variant GST according to the present invention and a second region comprising a polynucleotide encoding a protein or protein variant according to the present invention. In a further embodiment of the present invention said first region comprises a polynucleotide encoding the amino acid sequence depicted as SEQ ID No. 10 and said second region comprises a polynucleotide encoding the amino acid depicted as SEQ ID No. 1. The regions may be separated by a region which provides for a self processing polypeptide which is capable of separating the proteins such as the self processing polypeptide described in U.S. Pat. No. 5,846,767 or any similarly functioning element. Alternatively the regions may be separated by a sequence which acts as a target site for an external element which is capable of separating the protein sequences. Alternatively the polynucleotide may provide for a polyprotein which comprises a plurality of protein functions such as a GST and a homoglutathione synthetase according to the invention. In a further embodiment of the present invention the proteins of the polyprotein may be arranged in tandem. In a still further embodiment of the present invention the polyprotein comprises a plurality of protein functions which are separated by linker sequences.

The present invention still further provides a method of evolving a polynucleotide which encodes a GST protein which is capable of conferring resistance to a herbicide which comprises fomesafen and/or acifluorfen or a protein which is capable of catalysing the addition of Beta-alanine onto gamma glutamylcysteine (i.e. having such catalytic properties) comprising: (a) providing a population of variants of said polynucleotide and further polynucleotides which encode further proteins, at least one of which is in cell free form; and (b) shuffling said variants and further polynucleotides to form recombinant polynucleotides; and (c) selecting or screening for recombinant polynucleotides which have evolved towards encoding a protein having the said GST or said catalytic properties; and (d) repeating steps (b) and (c) with the recombinant polynucleotides according to step (c) until an evolved polynucleotide which encodes a protein having insecticidal properties has been acquired wherein said population of variants in part (a) contains at least a polynucleotide encoding a GST or variant GST protein or a protein or protein variant as described above.

The present invention still further provides a method as described above wherein said population of variants in part (a) contains at least a polynucleotide encoding the protein depicted as SEQ ID No. 10 and said further polynucleotides in part (a) encode a protein depicted as SEQ ID No. 1. The methods for evolving a polynucleotide as described above are well known to the person skilled in the art and are described inter alia, in U.S. Pat. No. 5,811,238.

The present invention still further provides a polynucleotide obtainable or obtained by the methods described above and a protein encoded by any such polynucleotide.

The present invention still further provides a DNA construct comprising in sequence a plant operable promoter operably linked to a polynucleotide according to the present invention operably linked to a transcription termination region. In a further embodiment of the present invention the DNA construct further comprises a region or a plurality of regions which provide for the targeting of the protein product or products to a particular location or locations. The DNA construct may to further comprise a region which provides for the production of a protein which acts as a selectable marker. The selectable marker may, in particular, confer resistance to kanamycin; hygromycin or gentamycin. Further suitable selectable markers include genes which confer resistance to other herbicides such as glyphosate based herbicides or resistance to toxins such as eutypine. Other forms of selection are also available such as hormone based selection systems such as the Multi Auto Transformation (MAT) system of Hiroyrasu Ebinuma et al. 1997. PNAS Vol. 94 pp2117–2121; visual selection systems which use the known green fluorescence protein, β glucoronidase and any other selection system such as mannose isomerase, xylose isomerase and 2-deoxyglucose (2-DOG). The plant operable promoter of the DNA construct may be selected from the group consisting of *Agrobacterium rhizogenes* Ro1D; Ro1D/Fd; potato protease inhibitor II; CaMV35S; CamV35S double enhanced; FMV35S; NOS; OCS; Patatin E9; alcA/alcR switch; GST switch; RMS switch; oleosin; ribulose bisphosphate carboxylase-oxygenase small sub-unit promoter. Terminators which can be used in the constructs according to the present invention include Nos, proteinase inhibitor II and the terminator of a gene of alpha-tubulin (EP-A 652,286). It is equally possible to use, in association with the promoter regulation sequence, other regulation sequences which are situated between the promoter and the sequence encoding the protein according to the present invention, such as transcriptional or translational enhancers, for example, tobacco etch virus (TEV) translation activator described in International Patent application, PCT publication number WO87/07644 or the Glucanase II leader sequence. The polynucleotide encoding the protein according to the invention may also be codon-optimised, or otherwise altered to enhance for example, transcription once it is incorporated into plant material. Such codon optimisation may also be used to alter the predicted secondary structure of the RNA transcript produced in any transformed cell, or to destroy cryptic RNA instability elements present in the unaltered transcript, thereby increasing the stability and/or availability of the transcript in the transformed cell (Abler and Green. 1996. Plant Molecular Biology (32) pp63–78).

The present invention still further provides a method of providing plants which are resistant and/or tolerant to an agrochemical comprising: (a) inserting into the genome of plant material a polynucleotide or a polynucleotide sequence which provides for a GST or variant GST as described above or a DNA construct as described above; and (b) regenerating plants or plant parts therefrom; and (c) applying to said plants or plant parts an amount of said agrochemical which is phytotoxic to control-like plants and selecting those plants or plant parts which are resistant to said agrochemical. In a further embodiment of the present invention the polynucleotide inserted into plant material in accordance with the method of the preceding sentence encodes an amino acid sequence depicted as SEQ ID No. 10. The present invention still further provides a method of providing plants which are resistant and/or tolerant to an agrochemical comprising: (a) inserting into the genome of plant material from a plant which provides for the production of a functional GST, a polynucleotide encoding a protein or variant which is capable of catalysing the addition of Beta-alanine onto gamma glutamylcysteine as described above or a DNA construct as described above; and (b) regenerating plants or plant parts therefrom; and (c) applying to said plants or plant parts an amount of said agrochemical which is phytotoxic to control like plants and selecting those plants or plant parts which are resistant to said agrochemical.

The present invention still further provides methods as described in the preceding paragraph wherein said agrochemical comprises fomesafen and/or acifluorfen. The polynucleotide/DNA construct may be incorporated into the genome of plant material in accordance with the present invention by plant transformation techniques which are well known to the person skilled in the art. Such techniques include but are not limited to particle mediated biolistic transformation, *Agrobacterium*-mediated transformation, protoplast transformation (optionally in the presence of polyethylene glycols); sonication of plant tissues, cells or protoplasts in a medium comprising the polynucleotide or vector; micro-insertion of the polynucleotide or vector into totipotent plant material (optionally employing the known silicon carbide "whiskers" technique), electroporation and the like. Techniques which are specifically optimised for a particular crop may also be employed for the purposes of transforming a particular crop in accordance with the present invention. For example, when transforming soybean it may be preferable to use a method based on one described by Christou et at (1990), Dan et at (1999), Williams et al (2000) and Hinchee et al (1999). The transformation method per se is not germane to the present invention and the skilled person may employ any functional method appropriate to the target crop.

The present invention still further provides herbicide resistant plants or plant parts obtained according to the methods described above. Such plants or plant parts may be selected from the group consisting of: melons; mangoes; soybean; cotton; tobacco; sugarbeet; oilseed rape; canola; flax; sunflower; potato; tomato; alfalfa; lettuce; maize; wheat; sorghum; rye; bananas; barley; oat; turf grass; forage grass; sugar cane; pea; field bean; rice; pine; poplar; apple; peaches; grape; strawberries; carrot; lettuce; cabbage; onion; citrus; cereal; nut plants or other horticultural crops. In a particular embodiment of the present invention said plants or plant parts are soybean (*Glycine* sp.) plants or plant parts.

The present invention still further provides the use of a polynucleotide encoding a GST or variant GST or a DNA construct as described above in a method of producing plants which are resistant and/or tolerant to a herbicide comprising fomesafen and/or acifluorfen.

The present invention still further provides a method of providing a plant with a further desired agronomic trait comprising: (a) inserting into the genome of plant material from a plant or plant part as described above a polynucleotide which provides for the desired agronomic trait; and regenerating plants or plant parts from said material; or (a) crossing a first plant or plant part as described above with a second plant which provides for said desired agronomic trait; and (b) selecting those resultant plants which contain said further desired agronomic trait. It will be appreciated that the plant resultant from such method will contain the characteristics of the GSTs and/or homoglutathione synthetase according to the present invention as described above along with the characteristics associated with said further agronomic trait. In a further embodiment of the present invention said further desired agronomic trait provides resistance to a herbicide which comprises glyphosate or a salt thereof. The further desired agronomic trait may also be selected from the group consisting of: further herbicide resistance; insect resistance; nematode resistance; stress tolerance; altered yield; altered nutritional value; altered quality or any other desirable agronomic trait. In a still further embodiment of the invention said further agronomic trait comprises resistance and/or tolerance to insects achieved via production of insecticidal proteins such as lectins or proteins derived from *Bacillus thuringiensis, Xenorhabdus* sp. and *Photorabdus* sp in the plant. In a still further embodiment of the invention said further agronomic trait comprises resistance and/or tolerance to nematodes achieved via production of nematicidal proteins such as enzyme inhibitors, in the plant The present invention still further provides a method of selectively controlling weeds in a field said field comprising crop plants and weeds said method comprising applying to said field an agriculturally acceptable formulation of an agrochemical comprising fomesafen and/or acifluorfen wherein the said crop plants are the plants according to the invention.

The present invention still further provides the use of an agrochemical comprising fomesafen and/or acifluorfen to selectively control weeds in a field which field comprises crop plants and weeds comprising applying to said field an agriculturally acceptable formulation of said agrochemical in an amount which is sufficient to be phytotoxic to said weeds but hot said crop plants characterised in that said crop plants are the plants according to the invention.

In a further aspect of the present invention there is provided a protein comprising the sequence depicted as SEQ ID No. 10 or a protein variant having a Smith-Waterman score greater than 766 in the SWISSPROT database calculated using the FASTA3 algorithm wherein the said protein variant still encodes a Glutathione-S-transferase. In a further embodiment of the present invention said protein variant has a Smith-Waterman score greater than 770 in the SWISSPROT database calculated using the FASTA3 algorithm wherein the said protein variant still encodes a Glutathione-S-transferase. In a still further embodiment of the present invention said protein variant has a Smith-Waterman score greater than 780 in the SWISSPROT database calculated using the FASTA3 algorithm wherein the said protein variant still encodes a Glutathione-S-transferase. In a further embodiment of the present invention said protein variant has a Smith-Waterman score greater than 790 in the SWISSPROT database calculated using the FASTA3 algorithm wherein the said protein variant still encodes a Glutathione-S-transferase.

In a further aspect of the present invention there is provided a protein comprising the sequence depicted as SEQ ID No. 7 or a protein variant having a Smith-Waterman score greater than 1094 in the SWISSPROT database calculated using the FASTA3 algorithm wherein the said protein variant still encodes a glutathione-S-transferase.

In a still further aspect of the present invention there is provided a protein comprising the sequence depicted as SEQ ID No. 9 or a protein having a Smith-Waterman score greater than 671 in the SWISSPROT database calculated using the FASTA3 algorithm wherein the said protein variant still encodes a Glutathione-S-transferase. The Fasta algorithm referred to above is well known to the skilled artisan and uses the method of Pearson and Lipman (Proc. Natl. Acad. Sci. USA 85; 2444–2448 (1988)) to search for similarities between one sequence and any group of sequences of the same type as the query sequence. Fasta also determines the best segment of similarity between the query sequence and the sequences in the database using a variation of the Smith-Waterman algorithm. This "local alignment" procedure is described in Chao, Pearson, and Miller (CABIOS 8; 481487 (1992)). The score for this alignment is reported as the opt and Smith-Waterman score. The database used in the above calculations is the SWISSPROT database. This database, which is well known and frequently used by the person skilled in the art is commercially available from sources such as Geneva Bioinformatics (GeneBio™) S.A 25 avenue de Champel CH-1206 Geneva Switzerland.

In a further aspect of the present invention there is provided a protein comprising the sequence depicted as SEQ ID No. 1 or a protein variant having a Smith-Waterman score greater than 2152 calculated using the FASTA3 algorithm wherein the said protein variant still encodes a homoglutathione synthetase. In a further embodiment of the present invention said protein variant has a Smith-Waterman score greater than 2159 calculated using the FASTA3 algorithm wherein the said protein variant still encodes a homoglutathione synthetase. In a still further embodiment of the present invention said protein variant has a Smith-Waterman score greater than 2169 calculated using the FASTA3 algorithm wherein the said protein variant still encodes a homoglutathione synthetase. In a still further embodiment of the present invention said protein variant has a Smith-Waterman score greater than 2971 calculated using the FASTA3 algorithm wherein the said protein variant still encodes a homoglutathione synthetase. The opt score can be calculated in accordance with the methods described above. The homoglutathione synthetase referred to above is also capable of catalysing the addition of Beta-alanine onto gamma glutamylcysteine.

The present invention still further provides a method of providing a plant which is tolerant to stress comprising incorporating a DNA encoding a GST or a variant GST according to the present invention into the genome of plant material such that a Glutathione-S-Transferase enzyme is produced wherein said stress is induced by an agent selected from the group consisting of: Ozone; Potassium and Sodium salts; Temperature and Pathogens. Stress tolerant, increased stress tolerance, tolerance to stress and similar phrases used herein refer to the ability of a plant, or group of plants such as a field planted with a particular crop, that are transformed to contain the GST according to the invention as described above, to overcome or resist the effects of a stresser to a greater extent than control-like plants. Increased stress tolerance may vary from a slight increase in the ability to resist or overcome the effects of a stresser to total tolerance where the plant is unaffected by the stresser. Stress tolerant plants may show physical characteristics that indicate increased tolerance to an environmental stress. For example, plants that are transformed to contain the GSTs according to the invention may be larger than control-like plants when grown in the presence of a particular stresser such as hot or cold temperatures. In a particular embodiment the stress tolerant plants according to the invention will be able to tolerate temperatures of at least 1° C. higher or lower than the control-like plants. In a further embodiment said plants will be able to tolerate temperatures of at least 2° C. higher or lower than the control-like plants. In a still further embodiment said plants will be able to tolerate temperatures of at least 3° C. higher or lower than the control-like plants. In a still further embodiment said plants will be able to tolerate temperatures of at least 4° C. higher or lower than the control-like plants. In a still further embodiment said plants will be able to tolerate temperatures of at least 5° C. or more higher or lower than the control-like plants. Plants according to the invention may also be able to tolerate any such temperature for a longer time period than that of the control-like plant. Similarly, transformed plants may emerge sooner than non-transformed plants, or be able to grow in the presence of the stresser when the control-like plant is not able to grow under the same conditions. The affected traits of the plant will depend on the type of plant and stresser involved.

The present invention further provides the use of a GST or GST variant according to the invention as described above in a method of producing a plant having increased tolerance to a stress which stress is induced by an agent selected from the group consisting of: Ozone; Potassium and Sodium salts; Temperature and Pathogens. In a particular embodiment of the present invention the GST used in said method encodes the protein depicted as SEQ ID No. 10.

The present invention still further provides the use of a GST or variant GST as described above as a selectable marker gene. When used as a selectable marker the GST according to the invention will normally form part of a transformation construct which comprises a preferred gene of interest along with the selectable marker. When the desired material has been transformed, a selection pressure (created through application of a herbicide such as fomesafen and/or acifluorfen) is applied to the material to initiate and facilitate selection. Only those cells containing the selectable marker survive this step thereby reducing any regenerated material to that which contains the transformation construct. In a particular embodiment said GST comprises a sequence which encodes the amino acid sequence depicted as SEQ ID No. 10 or is a variant GST as described above and selection is achieved through the application of a herbicide which comprises fomesafen and/or acifluorfen at levels which are toxic to control-like material which does not comprise said GST in a similar amount. In a further embodiment of the invention the selection of cells which comprise said marker takes place when the cells have developed into embryogenic callus and/or somatic embryos.

Once in possession of the GSTs according to the invention the skilled artisan is quite capable of utilising them as selectable markers.

According to a further aspect of the present invention there is provided a GST protein which is capable of reacting with a monoclonal anitbody raised to the protein depicted as SEQ ID No. 10.

According to a further aspect of the present invention there is provided a GST protein which is capable of reacting with a monoclonal anitbody raised to the protein depicted as SEQ ID No. 1.

The invention will now be described by way of the following non-limiting examples with reference to the figures and sequence listing of which:

SEQUENCE LISTING

Figure 1:
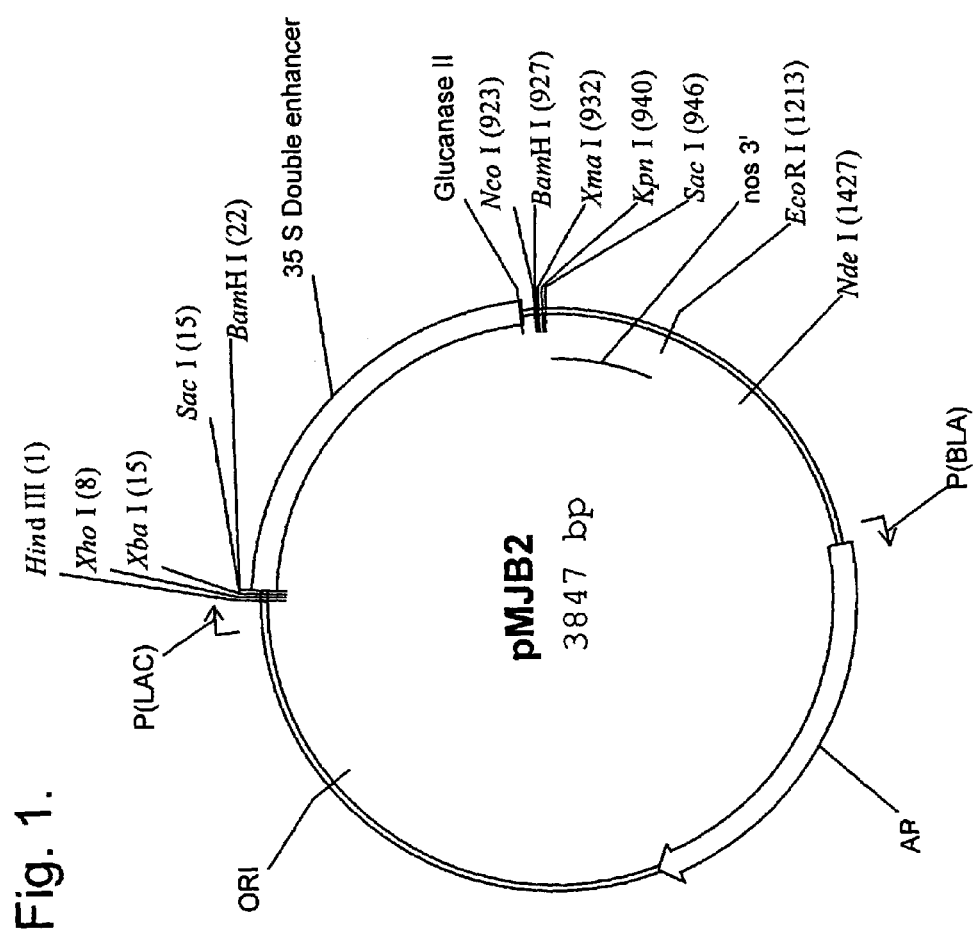
FIG. 1 shows a schematic diagram of cloning vector pMJB2.

SEQ ID No. 1. Homoglutathione synthetase from *Glycine max*.

SEQ ID Nos. 2 to 5. Homoglutathione synthetase protein regions.

SEQ ID No. 6. Polynucleotide sequence encoding Homoglutathione synthetase from *Glycine max*.

SEQ ID Nos. 7 to 10. Glutathione-S-transferases 2.6, 3.1, 3.2 and 3.3 respectively.

SEQ ID No. 11 to 14. Polynucleotides encoding the GSTs 2.6, 3.1, 3.2 and 3.3 respectively. (GST 3.3 may also be referred to as GST 3.6).

SEQ ID Nos. 15 to 24. Primers.

SEQ ID Nos. 25 to 34. Soybean sequence P32110 derived nucleic acid sequence;

Mungbean sequence U20809; Tobacco sequence Q03663; Potato sequence P32111 derived nucleic acid sequence; *Arabidopsis* sequence P46421; *Arabidopsis* sequence P46421 (genomic); Papaya sequence AJ000923; Spruce sequence AF051214; Wheat sequence AF004358; Spruce sequence AF051238 respectively.

SEQ ID No. 35. Primer.

SEQ ID Nos 36 to 43. Sequences of clones listed as SEQ ID Nos. 8, 22, 7, 21, 31, 15, 23 and 25 in International Patent Application Publication Number WO00/18936.

EXAMPLE 1

Isolation and Identification of Partial cDNAs Encoding Soybean GSTs 1.1 Partial cDNAs encoding soybean GSTs were obtained using reverse-transcriptase polymerase chain reaction (RT-PCR) with degenerate oligonucleotide primers designed to regions conserved within known tau-class GSTs using alignment methods known within the art. Total RNA was obtained from soybean cell cultures (*Glycine max* cv. Mandarin) using TRIzoL™ reagent (Life Technologies™) according to the manufacturers guidelines. First-strand cDNA was obtained from 5 µg total RNA using oligonucleotide OG2 (SEQ ID No. 35) in conjunction with Superscript-II reverse transcriptase (Life Technologies™) using standard protocols provided by the manufacturer. Degenerate oligonucleotide primers CON2 (SEQ ID No. 17) and CON3 (SEQ ID No. 18) were then used in independent PCR reactions with oligonucleotide primer OG9 (SEQ ID No. 16) to amplify partial GST-encoding genes from first strand cDNA. 2 µl of the first-strand cDNA synthesised was used as template in the reaction. The PCR conditions used are (94° C., 45 s; 51° C., 30 s and 72° C., 60 s) 35 cycles using Taq DNA polymerase supplied by Life Technologies and a Techne™ thermocycler. The amplified products were ligated into the pCR2.1 vector (Invitrogen™ and transformed into *E. coli* INV F' cells.

1.2 Transformed colonies were selected on LB media containing 100 ug ml-1 ampicillin and 40 ug ml X-GAL. Plasmid was recovered from 5 ml overnight cultures, initiated from each of 90 individual white colonies (45 from each initial RT reaction). The various plasmids were then subjected to restriction analysis (EcoR1, Ssp1, Ssp1:Sph1 and Rsa1) allowing the grouping of similar clones to be made. Distinct cDNAs were identified by automated DNA sequencing with M13 primers, using an ABI 377 automated DNA sequencer, and analysed for similarity with known GST sequences by conducting database searches using the BLAST algorithm (Altschul S. F et al., 1990).

EXAMPLE 2

Isolation and Identification of Partial cDNA Encoding Homoglutathione Synthetase 2.1 A partial length cDNA encoding homoglutathione synthetase was obtained by RT-PCR. Degenerate oligonucleotide primers MS-3 (SEQ ID No. 15) and OG9 (SEQ ID No. 16) were used to specifically amplify the desired clone from first-strand cDNA, produced from soybean cell cultures as described previously.

2.2 The PCR product obtained was cloned into vector pCR2.1 and sequenced using an ABI377™ automated DNA sequencer. Products exhibiting homology to related glutathione synthetases were identified by searching the databases using the BLAST algorithm.

EXAMPLE 3

Library Construction, Clone Isolation and Sequencing 3.1 A cDNA library was constructed using the lambda ZAP-II system (Stratagene). Total RNA was isolated from 5-day-old soybean cell suspension cultures (cv Mandarin) using TRIzoL™ reagent. Poly A+ mRNA is isolated from total RNA using PolyATtract (Promega™) according to standard supplied protocols. The cDNA library was constructed following standard protocols provided by Stratagene™.

Table 1 below shows the characteristics of soybean cDNA library constructed from 5-day old soybean cell suspension cultures (cv. Mandarin).

| Library | Primary titre | Average cDNA size |
|---|---|---|
| Cell culture seedling | $2 \times 10^6$ pfu | 1.4 Kb |

3.2 The partial cDNA sequences identified in previous examples were $^{32}$P-labelled using a Ready-to-go labelling kit (Pharmacia™) and used to screen the soybean cDNA library for full-length cDNAs. 160,000 pfu's were screened and putative colonies cross-hybridising with the probes subjected to secondary and tertiary screening until plaque purity was observed. Plasmid DNA was recovered from the plaque pure stocks using in vivo excision protocols provided by Stratagene™. Full-length cDNAs encoding GSTs and a full length cDNA encoding the homoglutathione synthetase was identified

EXAMPLE 4

Identification of Soybean GSTs with Activity Toward Herbicide Substrates 4.1 Bacterial expression of cDNA clones Full length cDNAs encoding homoglutathione synthetase and glutathione S-transferase were independently expressed in *E. coli* using the pET expression system (Novagen™).

4.2 Nde I or Nco I sites were introduced as appropriate into the 5' end cDNAs encoding glutathione S-transferase and Bam H1 at the 3' end using PCR. The cDNA was then cloned into pET-24a or pET-24d as appropriate. The resulting plasmids were introduced into *E. coli* BL21 (DE3) using standard bacterial transformation procedures known to the skilled artisan. Expression and purification of the recombinant GST was performed using anion-exchange chromatography and S-Hexyl-glutathione affinity chromatography according to the methods known in the art (for example, Skipsey et al., 1997). GST activity of the purified recombinant protein toward CDNB, acetochlor, acifluorfen, chlorimuron-ethyl, fluorodifen. fomesafen and metolachlor in the presence of both glutathione and homoglutathione was performed via assays which are described in Andrews et al., 1997 and Skipsey et al., 1997.

4.3 Table 2 below shows activity of recombinant enzymes. ±SE, n=2, ND=Not detectable, * Activity nkat mg-1, ** Activity pkat mg-1

EXAMPLE 5

Identification of Active Homoglutathione Synthetase 5.1 Bacterial expression of cDNA clone.

A 5' Nco 1 and 3' Xho 1 restriction enzyme site were introduced into the homoglutathione synthetase cDNA via PCR using primers MS4-Nco (SEQ ID No. 19) and MS-4-HIS (SEQ ID No. 20). Additionally, the use of the MS4-HIS primer provided a C-terminal HIS-tag to assist purification of the enzyme.

5.2 The resulting PCR fragment was digested with Nco1 and Xho 1 and ligated into similarly digested pET-24d. This vector was termed pET-MS4-His. The purification of homoglutathione synthetase was performed using the following method. *E. coli* BL21 (DE3) harbouring the pET-MS4-His plasmid (section 1.3) were grown at 30° C. until $OD_{600}$=0.5, after which isopropyl-β-D-thiogalactoside (IPTG) was added to a final concentration of 0.1 mM. Following a 3 hour incubation the bacteria were collected by centrifugation, re-suspended in buffer A (20 mM Tris, 0.5 M NaCl, 5 mM imidazole pH 8.0) and lysed. Cell debris was removed by centrifugation (10,000 g, 10 min) and the supernatant applied to a 5 ml iminidiaceic acid column (Sigma™), previously charged with $NiSO_4$ and equilibrated in buffer A. The column was washed with buffer A containing 20 mM imidiazole, followed by buffer A containing 300 mM imidiazole to remove the affinity bound protein.

5.3 The eluted protein was concentrated using a Centriplus 30 (Amicon™) spin column and re-suspended in buffer A prior to application onto a 1 ml HiTrap chelating column (Phamacia™), pre-charged with $NiSO_4$ and equilibrated as described previously. Affinity bound protein was then recovered using an increasing concentration of 20–200 mM imidiazole and the presence of His-tagged recombinant homoglutathione synthetase was detected using His-tagged antibodies according to known procedures. Fractions containing recombinant homoglutathione synthetase were pooled, concentrated using Centricon 30 spin columns and re-suspended in 20 mM Tris-HCl pH 8.0, 1 mM DTT.

5.4 Homoglutathione synthetase was assayed for activity in 250 mM Tris-HCl pH 8.0, 50 mM KCl, 20 mM $MgCl_2$, 5 mM DTT, 10 mM ATP, 1 mM γ-glutamylcysteine and 50 mM glycine or 10 mM β-alanine in a total 100 μl. Experimental controls did not contain the enzyme or glycine/β-alanine. Assays were performed at 30° C. for 60 min, with 20 μl aliquots removed at regular time intervals. Monobromobimane derivatisation was then performed on the aliquot

TABLE 2

| Clone | GSH | hGSH | GSH | hGSH | GSH | hGSH | GSH | hGSH | GSH | hGSH | GSH | hGSH | GSH | hGSH |
|---|---|---|---|---|---|---|---|---|---|---|---|---|---|---|
| GST 2.6 | 18.7 ± 2.6 | 19.0 ± 0 | 352.5 ± 106.5 | 391.0 ± 12.0 | ND | 31.1 ± 0 | ND | ND | ND | 19.3 ± 2.8 | 27.1 ± 1.4 | 350.5 ± 78 | 142.0 ± 15.0 | 95.5 ± 12.5 |
| GST 3.1 | 59.2 ± 0 | 59.2 ± 0 | 190.5 ± 13.5 | 11.0 ± 2.5 | 152.5 ± 1.5 | 238.5 ± 2.5 | ND | ND | 1150 ± 50 | 1350 ± 0 | 213.6 ± 2.6 | 484.6 ± 11.8 | 177.5 ± 7.5 | 67.5 ± 1.5 |
| GST 3.2 | 24.9 ± 2.3 | 10.3 ± 1.6 | 418.0 ± 15.0 | 143.0 ± 18.0 | 7.5 ± 0.4 | 23.2 ± 0.1 | ND | ND | 78.2 ± 1.4 | 68.0 ± 4.3 | 21.3 ± 7.0 | 201.6 ± 2.7 | 253.0 ± 56.0 | 191.5 ± 1.5 |
| GST 3.3 | 82.9 ± 4.2 | 189.0 ± 9.7 | 420.0 ± 30.0 | ND | 123.0 ± 2.0 | 1350 ± 31 | ND | ND | 360.5 ± 48.5 | 602.5 ± 100.5 | 110 ± 3.0 | 6250 ± 150 | 312.0 ± 3.0 | 264.5 ± 8.5 | to determine the presence of either glutathione or homoglutathione in accordance with the methods described by Cummins et al., 1997.

TABLE 3

Characteristics of recombinant homoglutathione synthetase.

|  | β-alanine | Glycine |
|---|---|---|
| Vmax (pkats/mg hGS) | 42250 ± 3173 | 3300 ± 341 |
| Km (mM) | 0.84 ± 0.19 | 54.9 ± 18.7 |

EXAMPLE 6

Generation of Herbicide Resistant/Tolerant Plants 6.1 Plants with increased tolerance to the herbicides acifluorfen and fomesafen were obtained by expression in the plant host of both the active soybean GST 3.3 and the homoglutathione synthetase to further increase levels of homoglutathione, required for the enhanced efficiency function of GST 3.3.

Figure 3:
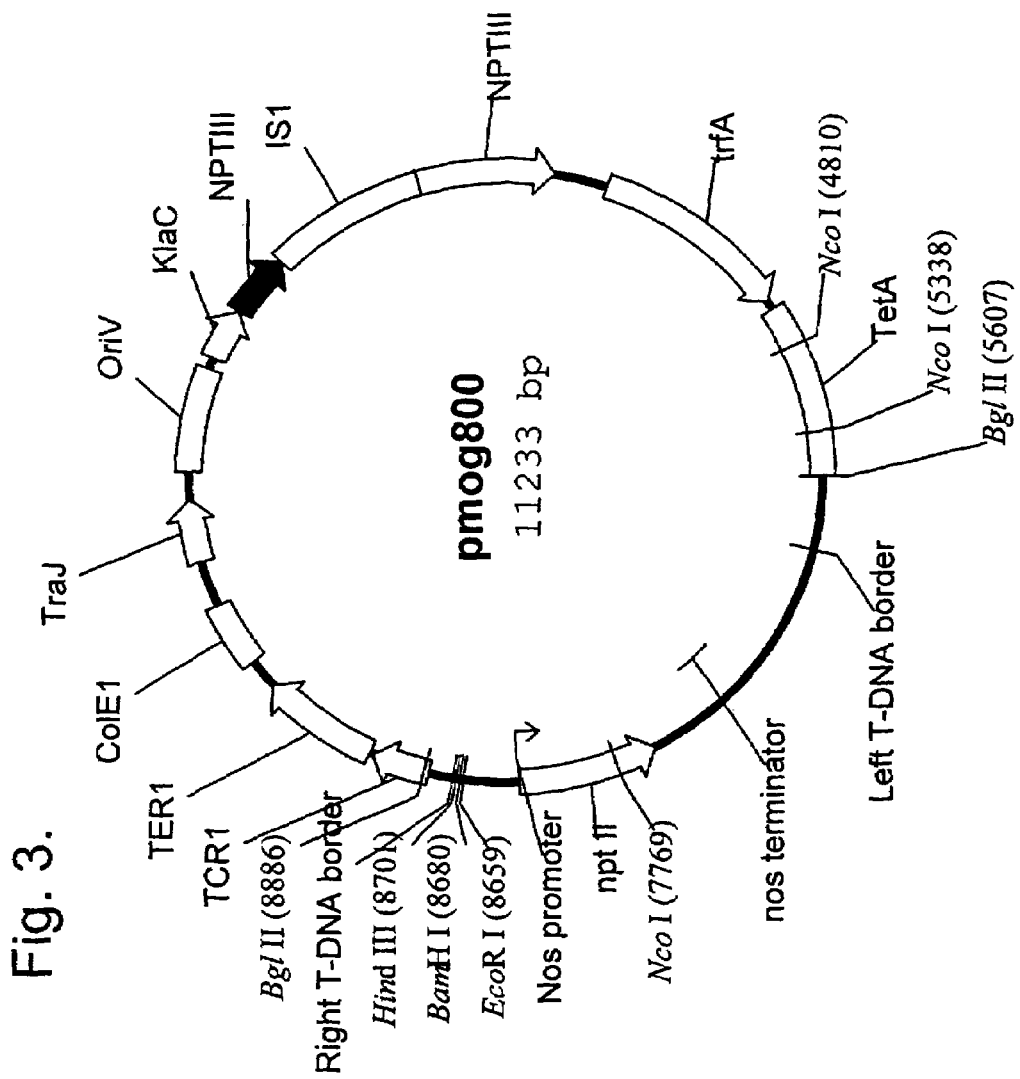
FIG. 3 shows a schematic diagram of binary vector pMOG800

6.2 PCR, using oligonucleotide primers hGSH-Nco1 (SEQ ID No. 21) and hGSH-Kpn1 (SEQ ID No.22) was used to introduce a 5' Nco1 site and 3' Kpn1 site into the GST 3.6 cDNA. The resulting PCR product was purified, sequenced, digested with Nco1 and Kpn1 and ligated into the vector pMJB2 (FIG. 1). The expression cassette, comprising the double enhanced CaMV35S promoter: Glucanase II leader, hGSH synthetase cDNA and nos terminator was then excised from pMJB2 using Hind I/EcoRI and ligated into the similarly digested binary vector pMOG800 (FIG. 3).

Figure 2:
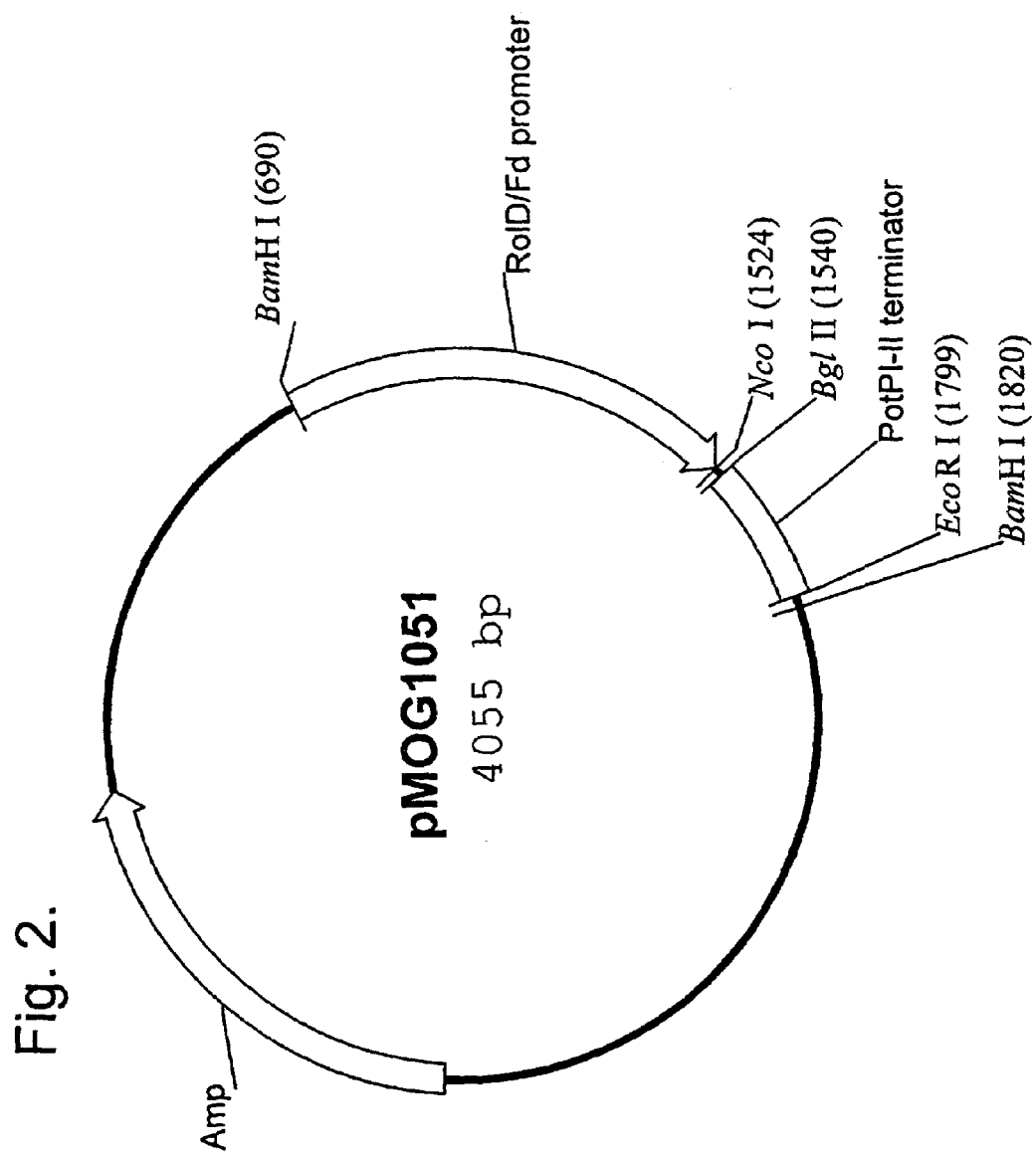
FIG. 2 shows a schematic diagram of cloning vector pMOG 1051
Figure 4:
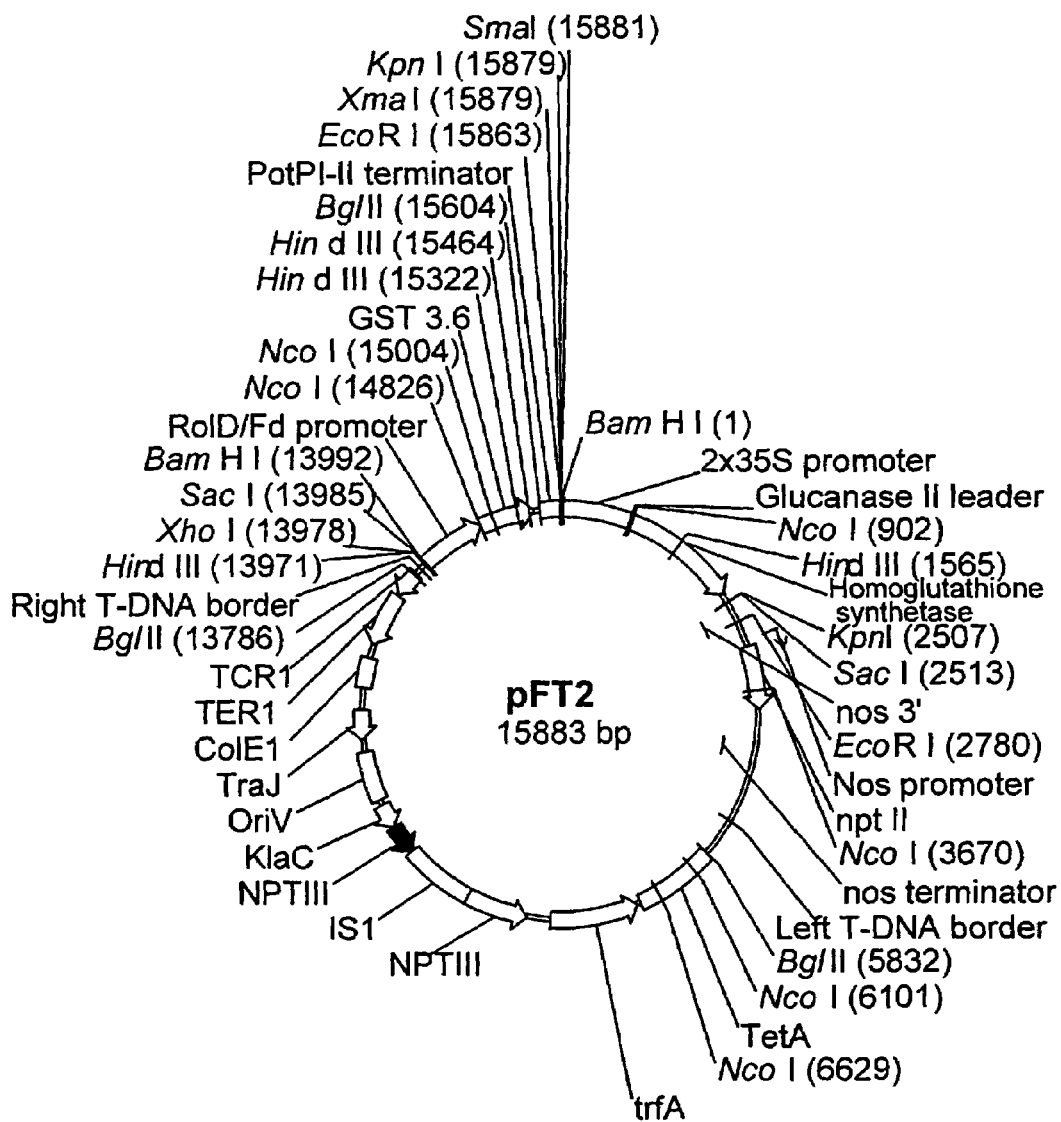
FIG. 4 shows a schematic diagram of vector pFT2 used, via *Agrobacterium* transformation, to transform plants to give resistance to herbicides.

6.3 Oligonucleotide primers 3.6-Bgl II (SEQ ID No. 23) and 3.6 Nco1 (SEQ ID No.24) were used to introduce Nco1 and Bgl II sites at the 5' and 3' end of the GST 3.6 cDNA respectively. The resulting PCR product was purified, sequenced, digested with Nco1 and Bgl II and sub-cloned into the vector pMOG 1051 (FIG. 2). The expression cassette, comprising the RolD/Fd promoter, GST 3.3 cDNA and potato PI-II terminator was then excised from pMOG1051 using Bam H1 and ligated into the unique Bam H1 site in the binary vector pMOG800 (FIG. 3) harbouring the homoglutathione synthetase expression cassette (see above). Orientation of the insert was determined by PCR. The resulting binary vector, termed pFT2 (FIG. 4) was sequenced in entirety to confirm authenticity.

EXAMPLE 7

Plant Transformation and Regeneration 7.1 The binary vector pFT2 was transformed into *Agrobacterium tumefaciens* strain LBA 4404 using the freeze thaw method of transformation provided by Holsters et al., 1978. Tobacco transformation and whole plant regeneration was performed using *Nicotiana tabacum* var. *Samsun* according to standard protocols detailed by Bevan, 1984. Transformation events were selected on MS-media containing kanamycin. Other transformation methods may be employed for the transformation of other crops, such as soybean. Examples of such methods are referred to below.

EXAMPLE 8

Analysis of Transgenic Plants 8.1 PCR analysis of Transformants

Leaf samples were taken from transformed lines and DNA extracted according to the methods described by Edwards et al., 1991. Oligonucleotide primer pairs SEQ ID No. 21 and SEQ ID No.22 and SEQ ID No.23 SEQ ID No.24 were used to amplify specific regions within the homoglutathione synthetase and GST 3.3 to enable the detection of both the transgenes within the putative transformed plant material. The following analyses were performed on PCR positive material in order to confirm the functionality of the introduced genes.

8.2 Enzyme Analysis

GST activity toward fomesafen in transgenic lines was performed in accordance with the methods described in the publication of Andrews et al., 1997.

8.3 Free Thiol Synthetase Activity

Glutathione and homoglutathione synthetase activities were determined in the transgenic lines using the assay described previously.

8.4 Free Thiol Determination

The presence of free thiol within the transgenic plants was determined using the method of monobromobimane derivatisation. Tissue (1 g) is weighed accurately, frozen in liquid nitrogen, ground to a fine powder and transferred to a clean tube containing 3 ml 0.1 M HCl. After incubation on ice for 30 min with occasional mixing, the slurry was transferred to an eppendorf tube and centrifuged (13,000 g, 3 min). Two 100 µl aliquots of supernatant were transferred to clean eppendorfs, and 10 µl water added to one and the other spiked with 1 mM glutathione or homoglutathione (10 µl). The free thiol present was reduced by adding 10 µl 1 M NaOH followed by 10 µl 1 M NaOH containing 20 mg ml $NaBH_4$ and the solution incubated for 10 min at room temperature.

8.4.1 The reaction was stopped by the addition of 120 µl 3.6 M HCl and the samples centrifuged (13,000 g, 5 min). The supernatant (100 µl) was transferred to a fresh tube and 10 µl 5 mg ml monobromobimane dissolved in acetonitrile added, followed by 5 µl of 35% v/v N-ethylmorpholine. The samples were placed in the dark for a period of 20 min, and the reaction stopped by the addition of 880 µl 5% acetic acid (5 ul v/v). A standard curve was prepared by derivatising glutathione or homoglutathione (0–20 mmol), and the S-bimane conjugates analysed by HPLC using methodology known in the art (Cummins et al., 1997).

EXAMPLE 9

Herbicide Tolerance Tests 9.1 Following tissue culture, kanamycin-resistant plantlets were transferred to 5 inch pots containing John Innes potting compost no. 3. The plants were allowed to develop to approximately the 10-leaf stage and fomesafen applied at 10 g ai ha$^{-1}$, formulated with non-ionic surfactant, to the aerial tissue using a track sprayer. Visual assessment of phytotoxicity/plant necrosis is performed 5 days post application.

TABLE 4

Analysis of transgenic tobacco lines.

| Plant line | % damage | GST activity towards fomesafen GSH | GST activity towards fomesafen hGSH | GSH activity | hGSH activity | ug GSH | UG hGSH |
|---|---|---|---|---|---|---|---|
| WT | 55 | 1.4 | 5.0 | 0.91 | ND | 71.3 | ND |
| T82 3740 | 15 | 5.2 | 558.5 | 4.6 | 113.3 | 78.3 | 18.5 |
| T82 3747 | 5 | 10.7 | 1320.4 | 1.59 | 145.9 | 112.2 | 26.9 |

EXAMPLE 10

Production of Homozygous Plant Lines 10.1 Single copy transgenic plant lines were identified by Southern blot analysis according to methods described by Sambrook, 1989 using appropriate radiolabelled probes. Segregation analysis was performed on plants containing single insertion events by germination on MS media containing kanamycin. Further confirmation of homozygous lines may be performed by back crossing transgenic lines with wild-type tobacco and analysis genetic segregation following selection on kanamycin.

REFERENCES

Altschul S. F., Gish W., Miller W., Myers E. U and Lipman D. J (1990). Basic local alignment tool. *Journal of Molecular Biology* 215 403–410.

Andrews C. J., Skipsey M., Townson J. K., Morris C., Jepson I. and Edwards R (1997) Glutathione transferase activities toward herbicides used selectively in soybean. *Pesticide Science* 51 213–222.

Bevan M. M (1984) Binary *Agrobacterium* vectors used for plant transformation. *Nucleic Acids Research* 12 8711–8721.

Cummins I., Moss S., Cole D. J and Edwards R (1997) Glutathione Transferases in Herbicide-resistant and Herbicide-Susceptible Black-grass (*Alopecurus myosuroides*). *Pesticide Science* 51 244–250.

Edwards K., Johnstone C and Thompson C (1991) A simple and rapid method for the preparation of plant genomic DNA for PCR analysis. *Nucleic Acids Research* 19 1349.

Holsters M., de Waele D., Depicker A., Messens E., van Montagu M and Schell J (1978) Transfection and transformation of *Agrobacterium tumefaciens*. *Molecular and General Genetics* 163 181–187.

Skipsey M., Andrews C. J., Townson J. K., Jepson I and Edwards R (1997) Substrate and thiol specificity of a stress-inducible glutathione transferase from soybean. *FEBS Letters* 409 370–374.

Christou, Paul. Physiol. Plant. (1990), 79(1), 210–12. Soybean transformation by electric discharge particle acceleration.

Dan, Yinghui; Reichert, Nancy A. (1999), U.S. Pat. No. 5,968,830 Soybean transformation and regeneration methods.

Williams, Edward J.; Emler, Carol A.; Julson, Lori S.; Martinell, Brian J.; Mccabe, Dennis E.; Huang, Yong. (2000) International Patent Application Publication Number. WO/0042207 Soybean transformation method omitting callus culture.

Hinchee, Maud Ann Wrightson; Clemente, Thomas Elmo; Connor-Ward, Dannette Vaudrilyn; Fedele, Mary Jacqueline; Fry, Joyce Ellen; Howe, Arlene R.; Rozman, Renee Jean. U.S. Pat. No. 5,959,179. Method for transforming soybeans.

The invention claimed is:

1. An isolated Glutathione-S-transferase (GST) comprising an amino acid sequence having at least 90% identity with SEQ ID NO: 10, wherein said GST has higher activity for conjugating homoglutathione to fomesafen and acifluorfen than for conjugating glutathione thereto.

2. The GST according to claim 1, wherein said GST is capable of conferring resistance or tolerance upon a plant to an herbicide which comprises at least one of fomesafen and acifluorfen.

3. The GST according to claim 1 comprising the amino acid sequence set forth in SEQ ID NO: 10.

* * * * *

SEQUENCE LISTING

<160> NUMBER OF SEQ ID NOS: 43

<210> SEQ ID NO 1
<211> LENGTH: 499
<212> TYPE: PRT
<213> ORGANISM: Glycine max

<400> SEQUENCE: 1

```
Met Ser Gln Pro Leu Thr Thr Asn Ser Val Leu Val Glu Glu Ala Ala
 1               5                  10                  15

Ala Asp Gly Asp Ser Ser Ala Ala Ala Pro Pro Leu Phe Asp Tyr His
                20                  25                  30

Arg Ile Asp Gln Lys Leu Leu Gln Asn Ile Val Tyr Asp Ala Leu Val
            35                  40                  45

Trp Ser Thr Leu Asn Cys Leu Leu Val Gly Asp Lys Ser Val Gln Arg
        50                  55                  60

Ser Gly Arg Val Pro Gly Val Gly Leu Val His Leu Pro Leu Ser Leu
    65                  70                  75                  80

Leu Pro Gly Pro Phe Pro Glu Ser His Trp Lys Gln Gly Cys Glu Leu
                85                  90                  95

Ala Pro Ile Phe Asn Glu Leu Val Asp Arg Val Ser Leu Asp Gly Lys
```

```
                100                 105                 110
Phe Leu Gln Glu Ser Leu Ser Arg Thr Lys Asn Ala Asp Glu Phe Thr
            115                 120                 125

Ser Arg Leu Leu Asp Ile His Ser Lys Met Leu Gln Ile Asn Lys Lys
130                 135                 140

Glu Asp Ile Arg Met Gly Ile Val Arg Ser Asp Tyr Met Ile Asp Glu
145                 150                 155                 160

Lys Thr Lys Ser Leu Leu Gln Ile Glu Met Asn Thr Ile Ser Thr Ser
                165                 170                 175

Phe Ala Leu Ile Gly Cys Leu Met Thr Gly Leu His Lys Ser Leu Leu
            180                 185                 190

Ser Gln Tyr Gly Lys Phe Leu Gly Leu Asn Ser Asn Arg Val Pro Ala
            195                 200                 205

Asn Asn Ala Val Asp Gln Ser Ala Glu Ala Leu Ala Lys Ala Trp Ser
210                 215                 220

Glu Tyr Asn Asn Pro Arg Ala Ala Ile Leu Val Val Gln Val Glu
225                 230                 235                 240

Glu Arg Asn Met Tyr Glu Gln His Tyr Ile Ser Ala Leu Leu Arg Glu
                245                 250                 255

Lys His His Ile Arg Ser Ile Arg Lys Thr Leu Thr Glu Ile Asp Gln
            260                 265                 270

Glu Gly Lys Ile Leu Pro Asp Gly Thr Leu Ser Val Asp Gly Gln Ala
            275                 280                 285

Ile Ser Val Val Tyr Phe Arg Ala Gly Tyr Thr Pro Lys Asp Tyr Pro
290                 295                 300

Ser Glu Ser Glu Trp Arg Ala Arg Leu Leu Met Glu Gln Ser Ser Ala
305                 310                 315                 320

Ile Lys Cys Pro Thr Ile Ser Tyr His Leu Val Gly Thr Lys Lys Ile
                325                 330                 335

Gln Gln Glu Leu Ala Lys Pro Gly Val Leu Glu Arg Phe Val Glu Asn
            340                 345                 350

Lys Asp His Ile Ala Lys Leu Arg Ala Cys Phe Ala Gly Leu Trp Ser
            355                 360                 365

Leu Glu Asp Ser Asp Ile Val Lys Lys Ala Ile Glu Asn Pro Glu Leu
370                 375                 380

Phe Val Met Lys Pro Gln Arg Glu Gly Gly Asn Asn Ile Tyr Gly
385                 390                 395                 400

Asp Glu Leu Arg Glu Thr Leu Leu Lys Leu Gln Glu Ala Gly Ser Gln
                405                 410                 415

Glu Asp Ala Ala Tyr Ile Leu Met Gln Arg Ile Phe Pro Ala Thr Ser
            420                 425                 430

Pro Ala Ile Leu Val Arg Asp Gly Asn Trp Asp Thr Gly His Val Ile
            435                 440                 445

Ser Glu Ala Gly Ile Phe Gly Thr Tyr Leu Arg Asn Lys Asp Lys Ile
            450                 455                 460

Ile Ile Asn Asn Glu Ser Gly Tyr Met Val Arg Thr Lys Ile Ser Ser
465                 470                 475                 480

Ser Tyr Glu Gly Gly Val Leu Pro Gly Phe Gly Val Val Asp Thr Val
                485                 490                 495

Tyr Leu Thr

<210> SEQ ID NO 2
<211> LENGTH: 10
```

-continued

```
<212> TYPE: PRT
<213> ORGANISM: Artificial Sequence
<220> FEATURE:
<223> OTHER INFORMATION: Description of Artificial Sequence:Protein
      Fragment

<400> SEQUENCE: 2

Lys Lys Ile Gln Gln Glu Leu Ala Lys Pro
  1               5                  10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:Protein
      Fragment

<400> SEQUENCE: 3

Cys Phe Ala Gly Leu Trp Ser Leu
  1               5

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence:Protein
      Fragment

<400> SEQUENCE: 4

Val Met Lys Pro Gln Arg Glu Gly Gly Gly Asn Asn Ile Tyr Gly
  1               5                  10                  15

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence:Protein
      Fragment

<400> SEQUENCE: 5

Ala Ala Tyr Ile Leu Met Gln Arg Ile Phe Pro
  1               5                  10

<210> SEQ ID NO 6
<211> LENGTH: 1854
<212> TYPE: DNA
<213> ORGANISM: Glycine max

<400> SEQUENCE: 6
ggcggcttgg tttgttctac ttcctcttac actgggatta gaacaaggcg tttgtgcact      60
tctaacaaca ccacctttcc cttcccccaa caacctcaat cactctcttt cgctaaacct    120
ctcaaactca tgtctcaacc tttgaccacc aactctgttc ttgttgaaga ggctgctgct    180
gatggtgatt cctccgccgc cgcacctccc ctcttcgatt atcatcgtat cgaccaaaaa    240
ctgctccaaa acatagttta cgatgctctt gtctggagca ccctcaactg cctccttgtt    300
ggtgacaaat ctgttcagag atcaggaaga gttcctggtg tgggcctggt acatctccca    360
ctttccttat tacctgggcc atttcctgaa agtcattgga agcaagggtg cgaattagct    420
cctatattta tgaacttgt tgatcgggtg agtttggatg ggaaatttct ccaggaatct    480
ctctccagaa ctaagaatgc ggatgaattt acctcaagac ttttagatat tcattctaag    540
```

-continued

```
atgctacaga ttaacaaaaa agaggacata cgcatgggaa tagttcgttc agattatatg    600
attgatgaga agactaaatc acttttacaa atagagatga acactatttc cacttcattt    660
gctttgattg gttgtcttat gactggactt cataagagct tactttctca atatggaaaa    720
ttccttggac taaattccaa tagggttcct gccaataatg ccgttgatca gtctgcagag    780
gccttggcta agcttggag tgagtataac aatcccaggg ctgcaattct ggtcgtggtt     840
caggttgaag aaagaaacat gtacgagcag cattatattt ctgcacttct aagagaaaag    900
catcatatta gaagcatacg caaaacgttg accgaaattg atcaggaagg aaaaattctg    960
ccagatggaa cactttctgt ggatggacaa gcaatttcag ttgtttactt ccgggctggc   1020
tacacgccaa aggactatcc ttcagaatca gaatggagag ctaggctact gatggaacaa   1080
tcttctgcta tcaaatgccc tacaatatct tatcatttgg ttggcaccaa aaagattcaa   1140
caggaacttg caaagcctgg tgttcttgag aggttcgttg aaaacaaaga ccacattgcc   1200
aaattgcgtg catgctttgc agggttgtgg agtttggaag actcagatat tgttaaaaaa   1260
gcaattgaaa atccagagct atttgtgatg aagcctcaaa gagaaggagg aggaaacaat   1320
atttatggtg atgagttgag ggaaaccctc cttaaattac aggaagcagg ttctcaagaa   1380
gatgcagcat acatccttat gcagaggata tttcccgcca cttctccagc aattttggtg   1440
cgtgatggta attgggatac gggtcatgtc atttcagaag ctggaatatt tggtacttat   1500
ttaaggaata aggacaagat tatcattaat aacgaaagtg gctatatggt gcgtacaaaa   1560
atatcatcat cttatgaagg aggagttttg cctggttttg gagtggtaga tactgtatac   1620
ctaacttgat ggagctaacc ccccaagtta tcaaagcaat tcaaaacatt atgtatggtt   1680
tatatatcac cactcaagtc tcctcactcc tgattttctt tgtatggagg cattgctgtt   1740
tcttttaatt gttcctatgg gatggtgtct aattattaac tgtactcaac gacctgtttg   1800
attctaacca ataaagattg atgaactgtt ctaacaaaaa aaaaaaaaaa aaaa          1854
```

<210> SEQ ID NO 7
<211> LENGTH: 222
<212> TYPE: PRT
<213> ORGANISM: Glycine max

<400> SEQUENCE: 7

```
Met Ser Ser Gln Glu Glu Val Thr Leu Leu Gly Val Val Gly Ser
 1               5                  10                  15

Pro Phe Leu His Arg Val Gln Ile Ala Leu Lys Leu Lys Gly Val Glu
                20                  25                  30

Tyr Lys Tyr Leu Glu Asp Asp Leu Asn Asn Lys Ser Asp Leu Leu Leu
            35                  40                  45

Lys Tyr Asn Pro Val Tyr Lys Met Ile Pro Val Leu Val His Asn Glu
        50                  55                  60

Lys Pro Ile Ser Glu Ser Leu Val Ile Val Glu Tyr Ile Asp Asp Thr
    65                  70                  75                  80

Trp Lys Asn Asn Pro Ile Leu Pro Ser Asp Pro Tyr Gln Arg Ala Leu
                85                  90                  95

Ala Arg Phe Trp Ala Lys Phe Ile Asp Asp Lys Cys Val Val Pro Ala
            100                 105                 110

Trp Lys Ser Ala Phe Met Thr Asp Glu Lys Glu Lys Ala Lys
            115                 120                 125

Glu Glu Leu Phe Glu Ala Leu Ser Phe Leu Glu Asn Glu Leu Lys Gly
    130                 135                 140
```

```
Lys Phe Phe Gly Gly Glu Glu Phe Gly Phe Val Asp Ile Ala Ala Val
145                 150                 155                 160

Leu Ile Pro Ile Ile Gln Glu Ile Ala Gly Leu Gln Leu Phe Thr Ser
                165                 170                 175

Glu Lys Phe Pro Lys Leu Ser Lys Trp Ser Gln Asp Phe His Asn His
            180                 185                 190

Pro Val Val Asn Glu Val Met Pro Pro Lys Asp Gln Leu Phe Ala Tyr
                195                 200                 205

Phe Lys Ala Arg Ala Gln Ser Phe Val Ala Lys Arg Lys Asn
210                 215                 220

<210> SEQ ID NO 8
<211> LENGTH: 235
<212> TYPE: PRT
<213> ORGANISM: Glycine max

<400> SEQUENCE: 8

Met Ala Glu Gln Asp Lys Val Ile Leu His Gly Met Trp Ala Ser Pro
1               5                   10                  15

Tyr Ala Lys Arg Val Glu Leu Ala Leu Asn Phe Lys Gly Ile Pro Tyr
                20                  25                  30

Glu Tyr Val Glu Glu Asp Leu Arg Asn Lys Ser Asp Leu Leu Leu Lys
            35                  40                  45

Tyr Asn Pro Val His Lys Lys Val Pro Val Leu Val His Asn Gly Lys
        50                  55                  60

Ala Ile Ala Glu Ser Met Val Ile Leu Glu Tyr Ile Asp Glu Thr Trp
65                  70                  75                  80

Lys Asp Gly Pro Lys Leu Leu Pro Ser Asp Ser Tyr Lys Arg Ala Gln
                85                  90                  95

Ala Arg Phe Trp Cys His Phe Ile Gln Asp Gln Leu Met Glu Ser Thr
                100                 105                 110

Phe Leu Val Val Lys Thr Asp Gly Glu Ala Gln Gln Lys Ala Ile Asp
            115                 120                 125

His Val Tyr Glu Lys Leu Lys Val Leu Glu Asp Gly Met Lys Thr Tyr
        130                 135                 140

Leu Gly Glu Gly Asn Ala Ile Ile Ser Gly Val Glu Asn Asn Phe Gly
145                 150                 155                 160

Ile Leu Asp Ile Val Phe Cys Ala Leu Tyr Gly Ala Tyr Lys Ala His
                165                 170                 175

Glu Glu Val Ile Gly Leu Lys Phe Ile Val Pro Glu Lys Phe Pro Val
            180                 185                 190

Leu Phe Ser Trp Leu Met Ala Ile Ala Glu Val Glu Ala Val Lys Ile
        195                 200                 205

Ala Thr Pro Pro His Glu Lys Thr Val Gly Ile Leu Gln Leu Phe Arg
210                 215                 220

Leu Ser Ala Leu Lys Ser Ser Ala Thr Glu
225                 230                 235

<210> SEQ ID NO 9
<211> LENGTH: 223
<212> TYPE: PRT
<213> ORGANISM: Glycine max

<400> SEQUENCE: 9

Met Ala Glu Val Lys Leu His Gly Phe Trp Tyr Ser Pro Tyr Thr Leu
1               5                   10                  15
```

```
Arg Val Val Trp Thr Leu Lys Leu Lys Asp Ile Pro Tyr Gln Asn Ile
            20                  25                  30

Glu Glu Asp Arg Tyr Asn Lys Ser Leu Gln Leu Leu Glu Tyr Asn Pro
            35                  40                  45

Val Tyr Lys Lys Thr Pro Val Leu Val His Asn Gly Lys Pro Leu Cys
            50                  55                  60

Glu Ser Met Leu Ile Val Glu Tyr Ile Asp Glu Ile Trp Ala His Asn
 65                  70                  75                  80

Ser Leu Leu Pro Ala Asp Pro Tyr Glu Arg Ala Leu Ala Arg Phe Trp
                85                  90                  95

Val Lys Tyr Ala Asp Asp Met Phe Ser Ala Val Ile Ala Phe Phe
            100                 105                 110

Leu Ser Asn Asn Asp Glu Glu Arg Glu Lys Ser Ile Glu Lys Ile Trp
            115                 120                 125

Glu His Leu Arg Val Val Glu Asn Gln Cys Phe Gly Asp Gln Lys Lys
130                 135                 140

Phe Phe Gly Gly Asp Ile Ile Asn Ile Met Asp Ile Ala Phe Gly Ser
145                 150                 155                 160

Ile Phe Lys Ile Leu Val Val Ala Glu Asp Ile Leu Asp Ala Lys Val
                165                 170                 175

Leu Glu Asp Glu Lys Phe Pro His Leu His Ser Trp Tyr Asn Asn Phe
            180                 185                 190

Lys Asp Val Ala Val Ile Lys Glu Asn Leu Pro Asp His Glu Lys Met
            195                 200                 205

Val Ala Phe Ala Lys Phe Ile Arg Glu Lys Arg Leu Ala Cys Thr
            210                 215                 220

<210> SEQ ID NO 10
<211> LENGTH: 232
<212> TYPE: PRT
<213> ORGANISM: Glycine max

<400> SEQUENCE: 10

Met Ala Glu Arg Asp Leu Arg Leu Leu Gly Ala Trp Phe Ser Pro Phe
 1               5                  10                  15

Ala Leu Arg Val Gln Ile Ala Leu Asn Leu Lys Gly Leu Asp Tyr Glu
            20                  25                  30

Val Val Glu Glu Thr Leu Asn Pro Lys Ser Glu Leu Leu Leu Lys Ser
            35                  40                  45

Asn Pro Val His Lys Lys Ile Pro Val Phe Phe His Gly Asp Lys Val
            50                  55                  60

Ile Cys Glu Ser Ala Ile Ile Val Glu Tyr Ile Asp Glu Val Trp Ser
 65                  70                  75                  80

Asn Asn Ala Leu Ser Ile Leu Pro Gln Asn Ala Tyr Asp Arg Ala Asn
                85                  90                  95

Ala Arg Phe Trp Val Ser Tyr Ile Asp Asp Lys Trp Leu Thr Ser Leu
            100                 105                 110

Lys Ser Val Leu Ala Thr Glu Asp Glu Ala Lys Lys Leu His Phe
            115                 120                 125

Glu Gln Ala Glu Glu Val Leu Glu Lys Val Glu Glu Val Phe Asn Lys
130                 135                 140

Cys Ser Glu Gly Lys Ala Tyr Phe Gly Gly Asp Thr Ile Gly Phe Val
145                 150                 155                 160

Asp Ile Gly Phe Gly Ser Phe Leu Ser Phe Ile Arg Val Ser Glu Asn
                165                 170                 175
```

```
Met Asn Glu Arg Lys Leu Leu Asp Glu Thr Lys Tyr Pro Gly Leu Thr
            180                 185                 190

Leu Trp Ala Glu Thr Phe Ala Ala Asp Pro Ala Val Lys Gly Leu Leu
        195                 200                 205

Pro Glu Thr Glu Lys Leu Val Glu Phe Ala Lys Ile Leu Gln Leu Lys
    210                 215                 220

Trp Ala Ala Ala Ala Ala Lys
225                 230

<210> SEQ ID NO 11
<211> LENGTH: 885
<212> TYPE: DNA
<213> ORGANISM: Glycine max

<400> SEQUENCE: 11
ctgcaatgtc ttcaagtcag gaagaggtga ccctttgggg agttgtggga agcccatttc      60
tacacagggt tcagattgct ctcaagttga agggagttga atacaaatat ttggaagacg     120
atttgaacaa caagagtgat ttgctcctca agtataaccc agtttacaaa atgattccag     180
tgcttgttca caatgagaag cccatttcag gtcccttgt gattgttgag tacattgatg      240
acacatggaa aaacaatccc atcttgcctt ctgatcccta ccaaagagcc ttggctcgtt     300
tctgggctaa gttcattgat gacaagtgtg tggttccagc atggaaatct gcttttatga     360
ctgatgagaa agagaaagag aaggctaaag aagagttatt tgaggctctg agtttcttg     420 agaatgagtt gaagggcaag ttttttggtg gagaggagtt tggctttgtg gatattgctg     480
ctgtgttaat acctataatt caagagatag cagggttgca attgttcaca agtgagaaat     540
tcccaaagct ctctaaatgg agccaagact ttcacaacca tccagttgtc aacgaagtta     600
tgcctcctaa ggatcaactt tttgcctatt tcaaggctcg ggctcaaagc ttcgttgcta     660
aaagaaagaa ttaatatagt gagactcaga atttccatcg aggtttcagt attgtatgaa     720
atgaaagcta cttgtctatg tttcgttatt gcggttgtat tttcatttt caatgaatta      780 tgtgatatag gatttctcca tgtcaaagaa tagttcaatt caatcaataa aataaacgaa     840
tgagtcgtgt tagagcaaaa aaaaaaaaaa aaaaaaaaa aaaaa                      885

<210> SEQ ID NO 12
<211> LENGTH: 899
<212> TYPE: DNA
<213> ORGANISM: Glycine max

<400> SEQUENCE: 12
atggcagagc aagacaaggt gatcctacac gggatgtggg ccagccctta tgccaagagg      60
gtggaattgg cccttaattt taagggcata ccctatgagt atgttgaaga agacttgaga     120
aataagagtg atttgcttct aaagtacaac cctgttcaca gaaaggttcc tgtacttgtt     180
cataatggaa aggccattgc tgaatccatg gtgatccttg agtatattga tgaaacatgg     240
aaagatggtc ctaaactgct tccaagtgat tcttacaaac gagcccaagc tcgattctgg     300
tgtcatttca tccaggatca gttaatggag agcactttttc tagtagtcaa aactgatgga     360
gaagcacaac aaaaggccat tgaccacgtg tatgagaaac tgaaagtgct agaagatgga     420
atgaagacct atctgggaga aggcaatgct attatctctg gtgttgaaaa caactttgga     480
atccttgaca ttgtgttttg tgcttttatat ggtgcctaca aggctcatga agaagttatt     540
ggcctcaagt tcatagtgcc agaaaagttt cctgtgttgt tttcttggtt gatggctatt     600
```

```
gctgaggttg aagctgtgaa aattgcaact cctccacatg aaaaaacagt gggaattctt        660
cagttgttca ggctgtctgc actgaaatct tcttctgcca cagaatgata tatacttcaa        720
cactttaata gactgtccat cgtttgcttc ttctgcgagt ctttaatgta tgtatctttc        780
aataacagga tgagtaacac ctgagtatgt aaagcgtgat gatatagaga tatacctcta        840
tatatcaaat actcttctat aaacacttct ttctttcctt aaaaaaaaaa aaaaaaaaa         899
```

<210> SEQ ID NO 13
<211> LENGTH: 840
<212> TYPE: DNA
<213> ORGANISM: Glycine max

<400> SEQUENCE: 13

```
atggcagagg tgaagcttca tggattttgg tatagtccct acactttgag ggtggtatgg         60
accttaaagt taaaggatat accatatcaa acatagaaag aagaccgcta caataagagt        120
cttcaacttc ttgaatacaa cccagtatac aagaaaactc cagtgcttgt ccataatgga        180
aaacccttat gtgagtccat gcttattgtt gaatacattg atgagatttg gcacataat         240 tcattacttc ctgctgatcc ctacgagaga gctctggcaa ggttttgggt taaatatgct        300
gatgatgaca tgttttctgc agttattgca ttcttcctta gcaataatga tgaagagcga        360
gaaaagagca tagagaagat atgggagcat ctcaggggttg ttgagaatca gtgttttggt        420
gatcagaaga aattttttgg gggagacatt attaacatta tggacatagc ttttgggtcc        480
atattcaaaa ttcttgtggt tgcagaagat attcttgacg cgaaggtcct ggaagatgag        540
aaattccctc acttgcattc atggtataat aatttcaagg atgttgcagt tattaaagaa        600
aacctcccag accatgagaa aatggtggct tttgctaagt ttattagaga aaaacgtttg        660
gcatgtacct aagaaagtaa tcttatatga gatcaagtat gaatcacttt gtatctgtct        720
gaatcgtttt gttatgcgtg tttctttagt ttccactcca ttattaggat gtcttgacat        780
atctgtgaaa gcaataaaag tttaatggga tgtactggat taaaaaaaaa aaaaaaaaaa        840
```

<210> SEQ ID NO 14
<211> LENGTH: 918
<212> TYPE: DNA
<213> ORGANISM: Glycine max

<400> SEQUENCE: 14

```
cataaaactc cacatttcct gctgagtaac ctaacaaaac aaacacaata ttgctccgtg         60
tttgacctgt tatagtaaac agtgatggct gaaagggact tgaggctttt gggtgcttgg        120
ttcagtccat ttgccctgag ggtgcagatt gcccttaacc tcaagggttt ggattatgag        180
gttgttgaag agactttgaa tcccaaaagt gaattgcttc ttagtccaa ccctgtgcac         240 aagaaaatcc cagttttctt ccatggagat aaagtcatat gtgaatctgc aatcatagtt        300
gagtacatag atgaggtttg gtccaacaat gctctctcca tccttccaca aaatgcatat        360
gatcgagcta atgcccgatt tgggttttct tacatcgatg acaagtggct tacgtccttg        420 aaagtgttc tagcgactga agatgatgag gcaagaagc tacactttga gcaagcggaa        480
gaagtgcttg agaaggtgga agaagtgttc aacagtgca gtgaagggaa ggcctatttc        540
ggaggagata cgattggatt tgttgacatt ggttttggaa gcttttgag tttcattaga        600 gtctcagaga atatgaatga agaaaattg cttgatgaaa cgaagtaccc tggtttgacc        660
ctatgggctg aaacttttgc tgctgatcct gctgtgaagg gccttctgcc agagactgaa        720
aagcttgttg agtttgcaaa gattcttcag ctaaaatggg ctgctgcagc tgctgcaaag        780
```

-continued

```
taaatggaat caaattaatt gctggatgaa tttcaaaaat tgttgtgcaa gttatttata      840
tctgaggcta tgtttgttgc aactttatat atttaaaagt caaataaat gttatgataa      900 tatagtaaaa aaaaaaaa                                                    918
```

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:PRIMER

<400> SEQUENCE: 15

```
gcgaagcchc armgagargg hggagg                                           26
```

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:PRIMER

<400> SEQUENCE: 16

```
cgcactgaga gaggatcctc gag                                              23
```

<210> SEQ ID NO 17
<211> LENGTH: 27
<212> TYPE: DNA
<213> ORGANISM: Artificial Sequence
<220> FEATURE:
<221> NAME/KEY: modified base
<222> LOCATION: n=a or t or g or c
<223> OTHER INFORMATION: Description of Artificial Sequence:PRIMER

<400> SEQUENCE: 17

```
ttctgggykr astwcntyga cranaag                                          27
```

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:PRIMER

<400> SEQUENCE: 18

```
gagtcymwkg tsattgttga atacattgat gag                                   33
```

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:PRIMER

<400> SEQUENCE: 19

```
cctctcaaac ccatggctca acc                                              23
```

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:PRIMER

<400> SEQUENCE: 20

-continued

| | |
|---|---|
| gcgctcgaga gttaggtata cagtatctac c | 31 |

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:PRIMER

<400> SEQUENCE: 21

| | |
|---|---|
| cctctcaaac ccatggctca acc | 23 |

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 22

| | |
|---|---|
| cgcggtacct ccatacaaag aaaatca | 27 |

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 23

| | |
|---|---|
| gagatctgca acaaacatag cctc | 24 |

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 24

| | |
|---|---|
| tacaccatgg ctgaaaggga cttg | 24 |

<210> SEQ ID NO 25
<211> LENGTH: 2763
<212> TYPE: DNA
<213> ORGANISM: Artificial Sequence
<220> FEATURE:
<223> OTHER INFORMATION: Description of Artificial Sequence:SOYBEAN
    Derived nucleic acid sequence P32110

<400> SEQUENCE: 25

| | |
|---|---|
| ccatacaaac aatacataac taaataactg taatttatg ttttctttca ttgtattgtg | 60 |
| cgttttatat taatgtatta attatgttgt tttttaattt ttattgataa attatttaaa | 120 |
| ctttaaataa aaaacattta aagtaaaacta taataaaaat atatataaca tgttttaaat | 180 |
| aattaaacat taaataaaa taataacata tcaaataaaa tcacaaaaaa tatactaatg | 240 |
| aaatcaactt aatattattt attatatatt taaatatata ttttttaact tttttatttt | 300 |
| aaaaaaataa aattgttaac attataaaat taaaaaacaa atttatgaaa aaaaaggtta | 360 |
| acaaattaaa aacaaactac aaatagtaaa ataacgtttt taaaaaaaaa aggaggttac | 420 |
| gatctcaaaa tcgtatacct catgaaattt ttaaaaaata agtaagacag ttttacaact | 480 |
| ttaaagtaat aaaacaaaat acgagttttt ttttaatacg actttaaagt cgtaaaaaaa | 540 |

```
ttatatttac attgaagttg taaataatat ttttacgatt tcagttaaaa aaataagaaa       600
actaaaaagt cgtaataggt gctaacaact gttacaactt aacccgtttt agataatttt       660
ttaaaatata ccccaaatga aaaattgcgg attatttat ccccaattgg taaaaaagca        720
cctgaatact agaaacaagg gtggcaaaga ttcaaagtaa tgaatttata aaaaaaaaaa       780
gaaatatttt atataattac acaaaatctt aaaaaatgtt gttattattt actactaatt      840
tataattcga atcgagtata tttaaggcaa agttctctac gcggtttacg taatctctta     900
catcatttat ttttccacgt ttgtttactc tgaggcatct tcttgatagg ggaaagtttt      960
ttcatatttt ttctagatcc ttctcatgtg caatgtctcc gcattcatac gcagcaatca     1020
aaatggaatt aatacacggt agcactttcc cattttttg ttatcgtccc cactattgac      1080
tatacccatg atatgtatat aggtatatct tttctaattg attacgtatc tgctgaatac     1140
tagctagtcc tgattcctag ctctataaaa ggagaatacc ataggaattc atcacagaca     1200
aacaaacaat ttaccagcta tacttgttcc ttttgaaggt tagaagtgct acaatacaaa     1260
caatggcagc tactcaggaa gatgtgaagc ttttgggtat tgtgggaagc ccatttgtgt     1320
gcagggtcca gattgcccctt aagttgaagg gagttaata caaattttg gaagaaaatt      1380 tgggcaacaa gagtgatttg cttctcaaat acaaccctgt tcacaagaag gttccagtgt    1440
ttgttcacaa tgagcagccc atagcagagt ctcttgtgat tgttgaatac attgatgaga     1500
catggaagaa caaccccatc ttaccttctg atccttacca aagagccttg gctcgtttct    1560
ggtccaaatt cattgatgat aaggtaactc aacatttcaa aaatcttctt agttttcatg    1620
atttgtgctg atttgtcagc aaaacatcac gatgaaatct atatatgtga aatctttctg    1680
gtgtggaata tatatgtgaa atctttgaat atgttagaga actcaaagt caacagccaa    1740 ccatgatttt tttttaatgt atcaacttttt tgtaaaacaa tattagtgat ttgaaacttt    1800
atggaatcat atactatgat tttgggagaa attttatttt attttactat ttttatctgg    1860
ggtgggggga ttctgtcacg tatttgtttc tatataactc gatctaaatt ctgtttgtcc     1920
taatcacttt atgaaataat tactaataaa tattgtgatt tgcgaaatca gattgtgggt    1980
gctgtatcga aatctgtttt cacggttgat gagaaagagc gtgagaagaa tgttgaagaa    2040
acatatgagg ctcttcagtt tcttgagaat gagctgaagg acaagaagtt ttttggagga    2100
gaggaatttg ggttggtaga tattgctgct gtcttcatag catttttggat cccaattttt    2160 caggaaatag cagggttgca gttattcacc agtgagaaat ttcctatact ctacaaatgg    2220
agccaagaat tccttaacca cccttttgtg cacgaagtcc ttcctcctag agacccactt    2280
tttgcctact tcaaagcccg ctatgaaagt ctttctgctt caaaatagac ttatttaagg    2340
atatttgttg aacaacttgt gtcttgttga gttattgctg tttgaatttc atgtaaaatg    2400
atactagcta tatgtaaatc ccagaaaaaa aaaaaaaga atcctaggat cttgttttcg    2460
ttttggccat ttcagtatat aaagaaatta tatttttcga tataaatttt gttgtgaaaa    2520
gctttattct tccttcataa aatccttcaa tgtgcataat cttattcgta gagagactta    2580
gagcggctag tagctactac cttgaaattt tttctttaat tcgaaggaca acgtatatat    2640
tatataataa taattattgc aagttggaaa tcgtgtaagc atgtttcatg actatatgag    2700
ttaacaatat actgtcttgc ctctgcaacc ttcatggatt ctaaaattat tcccttggct    2760
gca                                                                   2763
```

<210> SEQ ID NO 26
<211> LENGTH: 1137

-continued

```
<212> TYPE: DNA
<213> ORGANISM: Artificial Sequence
<220> FEATURE:
<223> OTHER INFORMATION: Description of Artificial Sequence:Mungbean
      Sequence U20809

<400> SEQUENCE: 26
gaattaaagt gcttcgatgg gttcaagtca ggaagaagtg acccttctgg aattattgga      60
agcccatttg tttgcagggt gaagatagcc ctgaagttga agggagttga atacaaatac     120
gttgaagaaa atttccgcaa caagagtgaa cagcttctga atacaaccc agttcacaag      180 aaggttccag tgtttgttca tggtgacaaa ccccttccag agtcccttgt gattgttgag     240
tacatcgatg agacatggaa caacaacccc atcttggctt ctgatcctta ccagagagcc     300
ttggctcgtt tctggtccaa attcatcgat gacaagattg tgggtgcttc gtggaaatct     360
gttttcacag ttgatgagaa agagcgtgag aagaatattg cagaaacata tgagagtctg     420
cagtttcttg agaatgagat aaaggagaag aagttctttg gaggagaaga gcttgggttg     480
gtagatattg ctgctgtcta tgtagcattt tggatcccctt tgattcaaga aatagcagga    540
ttggagttat tgacaagtga gaaatttcct aatctctaca ggtggagcca agaattttg     600 aaccatccaa ttgtcaaaga aagtcttccc cctagagacc cagttttttgc cttttttcaaa   660 ggacgctatg aaggcctttt tcttcgaaa tagatttcat gttgtgagag atttagaatt     720
tataaggaaa attgtgtgga gtacttagtt aggatttggt ttcaaaatta tggttgaagt     780
tgaatcctag gatttgcgca tgtcaaacaa ataacctggg attgttcgtg ttgatatttt     840
actatttcaa tcaataaatt atgcagcttc ttaccgagtt aacattcgat cgaaataagg     900
accaacaaga ttaagtaagg ctgcattatt tgtctttttg ttaaattaga tattagtatg     960
caccaaaaag tgagtatttc cttacagaag ctttttaaat attaagtagt taattccata    1020
ggtctaccat tatagctcaa gttatataca tattatgggt gccattctct actcaacaat    1080
tatgactata aaatcttgtg gttataatgc cacgaacaag tgaactatct cacttca       1137

<210> SEQ ID NO 27
<211> LENGTH: 2038
<212> TYPE: DNA
<213> ORGANISM: Artificial Sequence
<220> FEATURE:
<223> OTHER INFORMATION: Description of Artificial Sequence:Tobacco
      sequence Q03663

<400> SEQUENCE: 27
ctcgaggatt tcaaactcta gcttcactaa aacttgagct ttcttttcca ctaatgtcga     60
aaaacgaaat aaacataagc tatttacaaa aaataaaaaa atactccatt tgaatctaaa    120
gtcaagtcgt gattgggata agaaaataga aatttattta tactccagat caagccgtga    180
ttggaatgag ataatagaaa agtatgatag tacatgagta acatcaagtt ggaaattaag    240
ggaaggaaat tagagaaaga actgaagaat atccaaatat tctttacgtc caaatttgat    300
agttatttaa cgtcatcgag atgacggcca tgttcaagtt ttccacaaat attgagaaaa    360
gaaagaagaa gacacaaact gtgtttggta ttattatagt ttttttctttt agagaattga    420 ttgtacatat aagaaatata atataagatt tagaaataag attattagaa aaatcaaaca    480
tcaaagtatt tattttaaat tcttttttcca atggacattc ccattctgaa aaaaagaga    540 tataaatatg gaagtaaaaa ttaatcagat cgttaaatgt agaaaatatt aattaacaca    600
ttaaccataa ccagtctact ttatttaaca aaaagcacat ctgaratarc aaaaaagtgt    660
```

-continued

```
ttaacttcat gcattgacaa tttaaaatta ttttgcaaca tcgggtaaaa ctattttaca      720
acaattggta actgcatata taagtttaat atggtaacct agaaaatagg ataaattatc      780
tataacagga tatattacat tgatattacc atgtcaaaaa atttagtaag tacatgaata      840
atcaccgtga aatcttcaag atttctccta taaatacoct tggtagtaaa tctagttttt     900
ccattcaaga tacaacattt ctcctatagt catgggattt gttctctttt cacaattgcc     960
ttcatttctt cttgtctcta cacttctctt attcctagta atatcccact cttgccgtgc     1020
ccaaaattct caacaagact atttggatgc ccataacaca gctcgtgcag atgtaggtgt     1080
agaacctttg acctgggacg accaggtagc agcctatgcg caaaattatg cttcccaatt    1140
ggctgcagat tgtaacctcg tacattctca tggtcaatac ggcgaaaacc tagctgaggg    1200
aagtggcgat tcatgacgg ctgctaaggc tgttgagatg tgggtcgatg agaaacagta     1260
ttatgaccat gactcaaata cttgtgcaca aggacaggtg tgtggacact atactcaggt    1320
ggtttggcgt aactcggttc gtgttggatg tgctagggtt cagtgtaaca atggagaata    1380
tgttgtctct tgcaactatg atcctccagg taattataga ggcgaaagtc catactaatt    1440
gaaacgacct acgtccattt cacgttaata tgtatggatt gttctgcttg atatcaagaa    1500
cttaaataat tgctctaaaa agcaacttaa agtcaagtat atagtaatag tactatattt    1560
gtaatcctct gaagtggatc tataaaaaga ccaagtggtc ataattaagg ggaaaaatat    1620
gagttgatga tcagcttgat gtatgatctg atattattat gaacactttt gtactcatac    1680
gaatcatgtg ttgatggtct agctacttgc gatattacga gcaaaattct taactacatg    1740
ccttaggaac aagcttacac agttcatata atctactaga gggccaaaaa catgaaaatt    1800
accaatttag atggtaggag gatattgaaa gtggagcagc tagttttaat aactgaccgt    1860
tagtcttaaa attgacggta taaaaatatt tacataatca ggtcatttat aaggtaatta    1920
taggtaaata tttatgacga attctcaata gtaatctgaa aaaaaattgt aactaaccta    1980
ttatactaaa actactataa taggttagat tacattaatc atgtcattag aagatctt      2038
```

<210> SEQ ID NO 28
<211> LENGTH: 2796
<212> TYPE: DNA
<213> ORGANISM: Artificial Sequence
<220> FEATURE:
<223> OTHER INFORMATION: Description of Artificial Sequence:Potato-
     Derived nucleic acid sequence P32111

<400> SEQUENCE: 28

```
aagcttacat tcaacgtgtt gctgcttcaa aataagggtc tttacaaaat ttaaaaaata     60
taaagaagaa ttttgaattt tataattaaa gccgtcagaa aggacttgac ctttgaagcc    120
aacccaactc aatattagaa aatcaaaaat tttagtgcat tcatttataa aaaaaaaaaa    180
aattacttat gcagttcttg aacccttttgt gagacgagag ggagttgctc ggatggtaag    240
cacccttcac tttcaacccg aaggttgcga gtttgagtca ccaacggagc aaaaagggta    300
ggagctccta gaaagggtaa aaaaaaaaaa aaaattaat aaaaaaatac cctttatgaa      360
atttctcatt ccgctactgc acttctcccc tgatcttcct cgtgttttca attattaatt    420
ctatattcat gacaccatgt gatgtttctc tgggtagtcc taaaaatagg gtattgaaa     480 attatgttgt ttctctctgg tctatttact tttcttgtgt actttattgt atttcatatt    540
gttaattttt ggcttcgttt tataacatgt tattagcaca aaactttaat catatcgagt    600 taaacttttta attttgctta tcaacgtaaa agacaagata tgtgatcggc atgtataact    660
```

```
atgttttaat taggtataat acataaatat ttccttaat tttatctcat tttatattta      720
tgtcgtttaa ctttggagcg tacaagtgtc tacttgtgat ccagtaggtt atcaaagctg      780
gcatgcttag ttttactttc caaattgaaa tttatattag aattgaattc aggaagaatt      840
ttgtaggttc aactaaatta tatatatata tataaaaaaa taaaaattat tagacgcttc      900
gactatttac ttactttaaa atttgaattt tcgtacgaat aaaattattt gtcagagaaa      960
agtcttttag ctattcacat gctaggaagt ttcactttg gtggatcagt gattgtatat     1020
tatttaatat atatcaattt tctcatcaaa ctgaaaatga agataaaat taatattaaa      1080
aactccattc atttaattt attgtcatgt tttgacttga tccaaaatct aacaatttaa      1140
aaggttttaa atttttgtgc ttttttttaa attaaaaata tgtcaaatat attaaaatat     1200
attttttaaa ttttatacta aaaaacatgt cacatgaata tttgaaatta taaaattatc     1260
aaaaataaaa aagaatatt tctttaacaa attaaaatg aaaatatgat aaataaatta      1320
aactattcta tcattgattt ttctagccac cagatttgac caaacagtgg gtgacatgag     1380
cacataagtc atctttattg tatttatta ctcactccaa aaatataggg aatatgttta     1440
ctacttaatt tagtcaaata taattttata ttagaataat tgaatagtca aacaagaaac     1500
tttaatgcat ccttattttt tcctctataa aaaaagact agacaccaag ggagaccaac      1560
cacacataat taagatggca gaagtgaagt tgcttggtct aaggtatagt cctttagcc     1620
atagagttga atgggctcta aaaattaagg gagtgaaata tgaatttata gaggaagatt     1680
tacaaaataa gagccccttta cttcttcaat ctaatccaat tcacaagaaa attccagtgt     1740
taattcacaa tggcaagtgc atttgtgagt ctatggtcat tcttgaatac attgatgagg     1800
catttgaagg ccccttccatt ttgcctaaag acccttatga tcgcgcttta gcacgatttt     1860
gggctaaata cgtcgaagat aaggtatatt gcttttaagt tattccaatt gattgaaaag     1920
tttgttttag ttacgttatt acatatactt taggtctcat gcttttaat aatctttat      1980
aaaattcgac taagacgaac ttctcgtata gtcaacaata ctaacatatt tgtctagtag     2040
ttggttagga aataagttat ccgaatatta aattctggat aagtaatgaa taccatattt     2100
gatagttgat ttggagataa attattcgtg tataaaatta atatgatatt tgatttgcaa     2160
tttagaaata cataactatt ttatatgcat agatccatta taactaattg atatattatt     2220
aatatctgta taactctaac cagctatcga aacgagtcaa cgaaccttat taagttttgt     2280
ttgtttgggca gggggcagca gtgtggaaaa gtttctttttc gaaaggagag gaacaagaga     2340
aagctaaaga ggaagcttat gagatgttga aaattcttga taatgagttc aaggacaaga     2400
agtgctttgt tggtgacaaa tttggatttg ctgatattgt tgcaaatggt gcagcacttt     2460
atttgggaat tcttgaagaa gtatctggaa ttgttttggc aacaagtgaa aaatttccaa     2520
atttttgtgc ttggagagat gaatattgca cacaaaacga ggaatatttt ccttcaagag     2580
atgaattgct tatccgttac cgagcctaca ttcagcctgt tgatgcttca aaatgagtat     2640
acctcaagtg aatttcaaga ttttgtgtgg caataaaaat tgagttttg taaattcaat      2700
tgaaatatat taaagttgca tgttataaga tttatcttta tttcactagt taatataaat     2760
tttggattca cgtataaata aaagtattgt taagag                               2796
```

<210> SEQ ID NO 29
<211> LENGTH: 1289
<212> TYPE: DNA
<213> ORGANISM: Artificial Sequence
<220> FEATURE:
<223> OTHER INFORMATION: Description of Artificial Sequence:Arabidopsis -continued

P46421

<400> SEQUENCE: 29

```
aagtcaaggt acacatgctc cagggataag gcaaggttag gaattaggac acatctccac    60
ttactaaaaa agagataaaa aaaaattgta tagggaacgt tataaatatg ttgtaaagtc   120
aacatctgtt tccttctaga ctcttcgcat ttacatcaca ctgccgacca tataaaacgg   180
caaagttcgt cgtcgtttta tcacaagacc atcaacacca taaggctata aatccaagct   240
aaaaggtagt gattaactcc acaaaaccag aaaaactaca tttctaacat atagaagaaa   300
cagagaaaaa gagagagaga cccctaatgg ctgagaaaga agaagtgaag cttttgggga   360
tatgggcgag ccctttttagc cgtcgggtcg agatggctct caaactcaaa ggcataccgt   420
acgagtacgt ggaagagata ctggagaaca aaagcccttt gcttcttgct cttaacccta   480
ttcacaagaa agtccctgtt cttgtccaca atggtaaaac cattctcgag tctcatgtga   540
ttcttgaata catcgatgag acttggccac aaaatccaat tctccctcaa gatccttatg   600
aaagatccaa agctcgtttc tttgctaaac tcgtcgatga acaggtaatt gaattggttc   660
aaaattgcat gtcaaataat aaacaattgg ttctgctttg ttaatttatc aaacaagtaa   720
ttttctatta acattagcga ttatatgtct ctgtcattgt agattatgaa cgtgggggttt   780
atatcaatgg caagagcaga cgagaaagga agagaagttt tagccgagca ggtaagagaa   840
ctgattatgt atctcgagaa agaacttgtc ggaaaagatt acttcggagg caagactgtc   900
ggattcttgg actttgtcgc cggaagttta attccgtttt gtttggagag aggttgggaa   960
ggaataggat tggaagtgat tacagaggag aagtttccag agttcaagag atgggttagg  1020
aatttggaga aggttgagat tgttaaagat tgtgttccac caagagagga acatgtagaa  1080
cacatgaact atatggcaga gagagtgaga tcttcttaag aaaacaaatc atgtttagtt  1140
cttgatcatg caatgtttgt atggttatgt tgttgtttat tttattgaat atctttgtat  1200
gttgtgtggt tgagaagtga ggttttatca tcatctctca cgttatctta tttggtccca  1260
gccactattt agaattaatg gtaaagctt                                    1289
```

<210> SEQ ID NO 30
<211> LENGTH: 1339
<212> TYPE: DNA
<213> ORGANISM: Artificial Sequence
<220> FEATURE:
<223> OTHER INFORMATION: Description of Artificial Sequence:Arabidopsis Genomic sequence

<400> SEQUENCE: 30

```
gaattaattc ttgacgaagc atggggttgt cttcagaaaa tgaatggatc aagtcaaggt    60
acacatgctc cagggataag gcaaggttag gaattaggac acatctccac ttactaaaaa   120
agagataaaa aaaaattgta tagggaacgt tataaatatg ttgtaaagtc aacatctgtt   180
tccttctaga ctcttcgcat ttacatcaca ctgccgacca tataaaacgg caaagttcgt   240
cgtcgtttta tcacaagacc atcaacacca taaggctata aatccaagct aaaaggtagt   300
gattaactcc acaaaaccag aaaaactaca tttctaacat atagaagaaa cagagaaaaa   360
gagagagaga cccctaatgg ctgagaaaga agaagtgaag cttttgggga tatgggcgag   420
ccctttttagc cgtcgggtcg agatggctct caaactcaaa ggcataccgt acgagtacgt   480
ggaagagata ctggagaaca aaagcccttt gcttcttgct cttaacccta ttcacaagaa   540
agtccctgtt cttgtccaca atggtaaaac cattctcgag tctcatgtga ttcttgaata   600
```

```
catcgatgag acttggccac aaaatccaat tctccctcaa gatccttatg aaagatccaa      660
agctcgtttc tttgctaaac tcgtcgatga acaggtaatt gaattggttc aaaattgcat      720
gtcaaataat aaacaattgg ttctgctttg ttaatttatc aaacaagtaa ttttctatta      780
acattagcga ttatatgtct ctgtcattgt agattatgaa cgtggggttt atatcaatgg      840
caagagcaga cgagaaagga agagaagttt tagccgagca ggtaagagaa ctgattatgt      900
atctcgagaa agaacttgtc ggaaaagatt acttcggagg caagactgtc ggattcttgg      960
actttgtcgc cggaagttta attccgtttt gtttggagag aggttgggaa ggaataggat     1020
tggaagtgat tacagaggag aagtttccag agttcaagat atgggttagg aatttggaga     1080
aggttgagat tgttaaagat tgtgttccac caagagagga acatgtagaa cacatgaact     1140
atatggcaga gagagtgaga tcttcttaag aaaacaaatc atgtttagtt cttgatcatg     1200
caatgtttgt atggttatgt tgttgtttat tttattgaat atctttgtat gttgtgtggt     1260
tgagaagtga ggttttatca tcatctctca cgttatctta tttggtccca gccactattt     1320
agaattaatg gtaaagctt                                                  1339
```

<210> SEQ ID NO 31
<211> LENGTH: 968
<212> TYPE: DNA
<213> ORGANISM: Artificial Sequence
<220> FEATURE:
<223> OTHER INFORMATION: Description of Artificial Sequence:Papaya
    AJ000923

<400> SEQUENCE: 31

```
tagaactagt ggatcccccg ggctgcagga attcggcacg agagatttta tcttttagga       60
gctccgtttt acaacaatgg cggacgaggt tgttctcttg gatttctggc caagcccttt      120
tggaatgaga atcagaatcg ctttagccga gaagggtatt cactacgagt acaaggaaga      180
gaatctgaga aacaagagtc ccttactcct gcagatgaac ccggtacaca agaaaatccc      240
ggttctcatc cacaatggta aacccatctg tgagtctttg atccagattc agtacataga      300
tgaggtatgg agcgacaagg ctcctctgct tccctctgat ccttatcaga gagctcaagc      360
caggttctgg gctgactatg ttgacaagaa gatgtatgaa gctgggagga gagtttggac      420
gactaaaggg gaagaacagg aggggccaa gaaagagttc atagaaatct tgaagacttt      480
ggagggagaa cttggggaga agccttattt tggtggggaa agttttgggt atgtggattt      540 gactttttatc ccattctaca cttggttcag tgtgtatgaa agttttggga agatgagcat      600
agaggcagaa tgccccaagt tgtttagttg ggtgaaaagg tgtttggaga aggagagtgt      660
ttcaaaatct ctgcctgatc aagataaggt atacggcttc gttttggaac tcaggaaggc      720
tcttgggatt tgagtttttt gagagacttc aaaatccttg ttccatttcc attagggttc      780
gtcctccaag tattgattaa aaaaggttct ggatcaacta ctttatttgt ctagtctttt      840
actgttgtat tggaataaag gggtgtcctt ttgtggatta ggtgagattt ctatcaatat      900
tgtggtgacg tcaatttctt gtgtgttgta ggcaaatcat atttgaataa aatctttctt      960
tcatatgt                                                              968
```

<210> SEQ ID NO 32
<211> LENGTH: 1040
<212> TYPE: DNA
<213> ORGANISM: Artificial Sequence
<220> FEATURE:
<223> OTHER INFORMATION: Description of Artificial Sequence:Spruce
    AF051214

<400> SEQUENCE: 32

```
gaaaagacag atacatagaa agttagagac agttacaata cattttcaga gcaatcgcga      60
tggaggcctg tggagaagag gcgcaagtga agctgttggg tgggaatata agtcccttg     120
tgctgcgggt ccgtatagca cttgctctta aagggatcga ttacgagttc atcgaagaga    180
acatgcaaaa taagagccat ctgctgctgc aatcgaaccc tgttaacaag aagattccag    240
tgctcatcca caatggaaag cctgtttgtg agtccatgat tattgtgcag tacatagacg    300
aggcatggga cacgaaggcg ccagttctaa tgcccaaaga tccttatgac cgagccattg    360
cccgcttctg ggctgccttt gtagacgata agctgctgcc atgccttcgg ggagttttca    420
agggccaggg agagcagcaa cagaaagcgt tggaagaatc gggggcaagc tttcttttac    480
tggaggaggc tctgcgaacg agccactgct tctcgggaaa accgtatttc ggaggagatg    540
agatcggctt tcttgacatc gcattgggtg gtatgttagc atttgtcaaa gccctcgaga    600
aggttactaa tttagtttta atagaccagg agaagatgcc gctgttaagc acatggatga    660
atcgattctg tgaggccgat ggagtgaaag acgttatgcc ggatccggcc aagttgcagg    720
aatttatatc cgccatcaga gtcagattta catcaccacc tgctgccaat taggggaagc    780
cattcggcca ttaaatggat gttatcgtcc gcattgtttt tggttttatg ctgtcagttt    840
gaatgttgtt atgcttttg aattgttggt gtttaatggg aataattcta tcgcccaatc    900
tagcaccgtg tgattcgcta tcagttctca ccgtgttcca tgtaacttcg atttcatgat    960
tttgggagat agaacaaaaa ttcatggaaa tgtgtgttag tgttttatat ttgaaaaggg   1020
ttggatttgc agagaatgga                                               1040
```

<210> SEQ ID NO 33
<211> LENGTH: 902
<212> TYPE: DNA
<213> ORGANISM: Artificial Sequence
<220> FEATURE:
<223> OTHER INFORMATION: Description of Artificial Sequence:Wheat AF004358

<400> SEQUENCE: 33

```
ggcacgaggc aagcacaagc agctaaagca atctcagtgg tcttcaaaac acacacacac      60
acactgacac acatcgatcg aggtagttag agatggccgg aggagatgac ctgaagctgc    120
tcggcgcatg gccaagccca tttgttacca gggtgaagct ggcgctcgcc ctgaagggcc    180
tgagctacga ggacgtggag gaggacctgt acaagaagag tgagcttctc ctcaagtcca    240
acccggtgca caagaagata cccgtgctca tccacaacgg agccccggtc tgcgagtcca    300
tgatcattct ccagtacatc gacgaagtgt tcgccagcac cggcccgtcc cttcttccag    360
cggacccta cgagcgcgcc attgctcgct tctgggtggc ttacgttgac gacaagctgg    420
tagcccccatg gaggcagtgg ttgagggggca agacagagga ggagaaatcc gagggaaaga    480
agcaggcgtt cgccgcggtg ggggtcctcg aaggggccct gagggagtgc tccaagggag    540
gggcttctt cggtggcgac ggcgtcgggc tcgtcgacgt tgcgctggga ggcgtgctgt    600
cgtggatgaa ggtgaccgag gcgctgtctg gtgacaagat tttcgacgcc gccaagactc    660
cgctcctggc cgcatgggtg gagcgcttca ttgagctcga cgcggccaag gccgccctgc    720
cggacgtggg caggctgctt gagtttgcca aggcacgaga ggctgccgct gcagcgtcca    780
agtgagccgc cagcacatat ccagaataat taaaatttgt tattttaaat gttgtttgtt    840
cggctgcttg atgtaataat gtagtaactg atgtcgtcca tttaaaaaaa aaaaaaaaaa    900
```

```
aa                                                                          902

<210> SEQ ID NO 34
<211> LENGTH: 1127
<212> TYPE: DNA
<213> ORGANISM: Artificial Sequence
<220> FEATURE:
<223> OTHER INFORMATION: Description of Artificial Sequence:Spruce
      AF051238

<400> SEQUENCE: 34
gacacatata actcacaggc aaaaaaatat tcaattacaa tacattttcc gtgcaatggc         60
gacggaggct tgtggagaaa agggggcaagt gcagctgtta ggtgggagtc tgagttcctt       120
cgtgctgcgg gttcgcatag cacttgctct taaaggcatc gattacgagt tcatcgaaga       180
gaacatgcaa aataggagcc agctgctgct gcaatcaaac cctgttcaca ggaagattcc       240
agtgcttatc cacaatggaa agcccgtttg tgaatccatg attattgtgc agtacatcga       300
tgaggcatgg gacactaagg cacccaatct tatgcccaaa gatccatatg acctagccat       360
tgcccgcttc tgggctgcct ttgtagacga taagctcgtt ccatgtatgc ggagagtttt       420
cgctggccat ggcgagcagc tacagaaaga agcggaagat ctggttacaa actttcattt       480
gatagaggaa gctctgcgaa ccaacagctg cttctcagga aaagcgtatt ttggaggggga      540 taagataggc ttgcttgaca tcgcattggg tggtatgttg gcggttctca aaggcctcga       600
gaaggctacc gataccgtta aatagatcc ggagaagatg ccgttgctga gcgcatggat        660
ggaccgattt tgtcaatcca atggagtgaa agaagtaatg cccgatccgg ccaagcagct       720
ggaatctcta tcagctagga gagccagact tgcatcacct gctggcaatt agggcaagcc       780
atgtcggcct tataaactga ggatagacag atggattata aacttattat tcgtagtact       840 tgtccttta ttcatgtggt cagcttcagc gttttaattc ttgctgtttt atgtgaataa        900
gtctgaataa tgtttgggtg aatctcgcct gtactatagc tggcattcac ctgtttattg       960
tacgctgatt tagtttgaac aagttttggt gaatctcccc tgtactgaag ctggcattcc      1020
cctgttcaat gtgcgctgat ttagtttgaa taagtttttg atgaatctcg cttgtactgt      1080
agctatgtgc gatgatttt aatgccatag aaacgagaat gaaatgc                    1127

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 35
gagagaggat cctcgagttt tttttttttt tttt                                    34

<210> SEQ ID NO 36
<211> LENGTH: 234
<212> TYPE: PRT
<213> ORGANISM: Glycine max

<400> SEQUENCE: 36

Met Ser Lys Ser Glu Asp Leu Lys Leu Leu Gly Gly Trp Phe Ser Pro
  1               5                  10                  15

Phe Ala Leu Arg Val Gln Ile Ala Leu Asn Leu Lys Gly Leu Glu Tyr
             20                  25                  30

Glu Val Val Glu Glu Thr Leu Asn Pro Lys Ser Asp Leu Leu Leu Lys
```

```
                    35                  40                  45
Ser Asn Pro Val His Lys Lys Ile Pro Val Phe Phe His Gly Asp Lys
         50                  55                  60

Val Ile Cys Glu Ser Ala Ile Ile Val Glu Tyr Ile Asp Glu Ala Trp
 65                  70                  75                  80

Thr Asn Val Pro Ser Ile Leu Pro Gln Asn Ala Tyr Asp Arg Ala Asn
                 85                  90                  95

Ala Arg Phe Trp Phe Ala Tyr Ile Asp Glu Lys Trp Phe Thr Ser Leu
                100                 105                 110

Arg Ser Val Leu Val Ala Glu Asp Glu Ala Lys Lys Pro His Phe
                115                 120                 125

Glu Gln Ala Glu Glu Gly Leu Glu Arg Leu Glu Glu Val Phe Asn Lys
130                 135                 140

Tyr Ser Glu Gly Lys Ala Tyr Phe Gly Gly Asp Ser Ile Gly Phe Ile
145                 150                 155                 160

Asp Ile Gly Phe Gly Ser Phe Leu Ser Trp Met Arg Val Ile Glu Glu
                165                 170                 175

Met Ser Gly Arg Lys Leu Leu Asp Glu Lys His Pro Gly Leu Thr
                180                 185                 190

Gln Trp Ala Glu Thr Phe Ala Ala Asp Pro Ala Val Lys Gly Ile Leu
                195                 200                 205

Pro Glu Thr Asp Lys Leu Val Glu Phe Ala Lys Ile Leu Gln Leu Lys
                210                 215                 220

Trp Thr Ala Ala Ala Ala Ala Ala Lys
225                 230

<210> SEQ ID NO 37
<211> LENGTH: 222
<212> TYPE: PRT
<213> ORGANISM: Glycine max

<400> SEQUENCE: 37

Met Ala Ser Ser Gln Glu Glu Val Thr Leu Leu Gly Val Val Gly Ser
 1               5                  10                  15

Pro Phe Leu His Arg Val Gln Ile Ala Leu Lys Leu Lys Gly Val Glu
                 20                  25                  30

Tyr Lys Tyr Leu Glu Asp Asp Leu Asn Asn Lys Ser Asp Leu Leu Leu
             35                  40                  45

Lys Tyr Asn Pro Val Tyr Lys Met Ile Pro Val Leu Val His Asn Glu
 50                  55                  60

Lys Pro Ile Ser Glu Ser Leu Val Ile Val Glu Tyr Ile Asp Asp Thr
 65                  70                  75                  80

Trp Lys Asn Asn Pro Ile Leu Pro Ser Asp Pro Tyr Gln Arg Ala Leu
                 85                  90                  95

Ala Arg Phe Trp Ala Lys Phe Ile Asp Asp Lys Cys Val Val Pro Ala
                100                 105                 110

Trp Lys Ser Ala Phe Met Thr Asp Glu Lys Glu Lys Glu Lys Ala Lys
                115                 120                 125

Glu Glu Leu Phe Glu Ala Leu Ser Phe Leu Glu Asn Glu Leu Lys Gly
                130                 135                 140

Lys Phe Phe Gly Gly Glu Phe Gly Phe Val Asp Ile Ala Ala Val
145                 150                 155                 160

Leu Ile Pro Ile Ile Gln Glu Ile Ala Gly Leu Gln Leu Phe Thr Ser
                165                 170                 175
```

| Glu | Lys | Phe | Pro | Lys | Leu | Ser | Lys | Trp | Ser | Gln | Asp | Phe | His | Asn | His |
|---|---|---|---|---|---|---|---|---|---|---|---|---|---|---|---|
|  |  |  | 180 |  |  |  |  | 185 |  |  |  |  | 190 |  |  |

| Pro | Val | Val | Asn | Glu | Val | Met | Pro | Pro | Lys | Asp | Gln | Leu | Phe | Ala | Tyr |
|---|---|---|---|---|---|---|---|---|---|---|---|---|---|---|---|
|  |  | 195 |  |  |  |  | 200 |  |  |  |  | 205 |  |  |  |

| Phe | Lys | Ala | Arg | Ala | Gln | Ser | Phe | Val | Ala | Lys | Arg | Lys | Asn |
|---|---|---|---|---|---|---|---|---|---|---|---|---|---|
|  | 210 |  |  |  |  | 215 |  |  |  |  | 220 |  |  |

<210> SEQ ID NO 38
<211> LENGTH: 895
<212> TYPE: DNA
<213> ORGANISM: Glycine max

<400> SEQUENCE: 38

| cacaactttg | ccccttgta | aaacttctta | ttgtgatgtc | taaaagcgaa | gacttgaagc | 60 |
| ttttgggagg | ctggttcagc | ccatttgccc | tgagggtgca | gattgccctt | aacctcaagg | 120 |
| gtctagaata | tgaggttgtt | gaagagacct | tgaatcccaa | aagtgacctg | cttcttaagt | 180 |
| ccaaccctgt | gcacaagaaa | atcccagttt | tcttccatgg | agataaagtc | atttgtgaat | 240 |
| ctgcaatcat | agttgagtac | attgatgagg | cttggactaa | tgttccctcc | atccttccac | 300 |
| aaaatgctta | tgatcgtgct | aatgctcgat | tttggtttgc | ctacattgat | gagaagtggt | 360 |
| ttacgtcctt | gagaagtgtt | ctagtggctg | aagatgatga | ggcaaagaag | ccacactttg | 420 |
| agcaagcaga | agaagggctt | gagaggttgg | aagaagtgtt | caacaagtac | agtgaaggga | 480 |
| aggcctattt | cggaggagat | agcattggat | tcattgacat | tggttttggg | agcttcttga | 540 |
| gttggatgag | agtcatagag | gagatgagtg | aagaaaaatt | gcttgatgaa | agaagcacc | 600 |
| ctggttttgac | ccaatgggct | gaaacgtttg | ctgctgatcc | tgctgtgaag | ggcattcttc | 660 |
| cagagactga | taagcttgtt | gagtttgcca | agattcttca | gctaaaatgg | actgctgcag | 720 |
| cagctgcagc | tgcaaagtaa | atggaatcaa | attaattgcg | agagtatttt | caaaattgtt | 780 |
| gtccaagttg | tttttatctc | aggctatgtt | gttgcaactt | tatttattta | aaagttattt | 840 |
| taaatttaaa | atgtaaaata | ttaagaaagt | ttaagtaagt | tagttgaaaa | atttt | 895 |

<210> SEQ ID NO 39
<211> LENGTH: 895
<212> TYPE: DNA
<213> ORGANISM: Glycine max

<400> SEQUENCE: 39

| aaataagtat | cttcgtagtt | gcataagtca | agagaagaag | tgaagtggct | gcaatggctt | 60 |
| caagtcagga | agaggtgacc | cttttgggag | ttgtgggaag | cccatttcta | cacagggttc | 120 |
| agattgctct | caagttgaag | ggagttgaat | acaaatattt | ggaagacgat | ttgaacaaca | 180 |
| agagtgattt | gctcctcaag | tataacccag | tttacaaaat | gattccagtg | cttgttcaca | 240 |
| atgagaagcc | catttcagag | tcccttgtga | ttgttgagta | cattgatgac | acatggaaaa | 300 |
| acaatcccat | cttgccttct | gatccctacc | aaagagcctt | ggctcgtttc | tgggctaagt | 360 |
| tcattgatga | caagtgtgtg | gttccagcat | ggaaatctgc | ttttatgact | gatgagaaag | 420 |
| agaaagagaa | ggctaaagaa | gagttatttg | aggctctgag | ttttcttgag | aatgagttga | 480 |
| agggcaagtt | ttttggtgga | gaggagtttg | gctttgtgga | tattgctgct | gtgttaatac | 540 |
| ctataattca | agagatagca | gggttgcaat | tgttcacaag | tgagaaattc | ccaaagctct | 600 |
| ctaaatggag | ccaagacttt | cacaaccatc | cagttgtcaa | cgaagttatg | cctcctaagg | 660 |
| atcaacttttt | tgcctatttc | aaggctcggg | ctcaaagctt | cgttgctaaa | agaaagaatt | 720 |

-continued

| | |
|---|---|
| aatatagtga gactcagaat ttccatcgag gtttcagtat tgtatgaaat gaaagctact | 780 |
| tgtctatgtt tcgttattgc ggttgtattt tcatttttca atgaattatg tgatatagga | 840 |
| tttctccatg tcaaaagata gttcaattca atcaataaaa taaacgaatg agcgg | 895 |

<210> SEQ ID NO 40
<211> LENGTH: 977
<212> TYPE: DNA
<213> ORGANISM: Glycine max

<400> SEQUENCE: 40

| | |
|---|---|
| ctgattcccg gctcaataag aggagaatac cttaggaatc cataagaaac attaattcac | 60 |
| cactatagtt gttctgttag aagtgctaca acaacaatg ctgctaatc aggaagatgt | 120 |
| gaagcttttg ggagctactg gaagcccatt tgtgtgcagg gttcagattg ccctcaagtt | 180 |
| gaagggagtt caatacaaat ttttggaaga aaatttgagg aacaagagtg aactgcttct | 240 |
| caaatccaac ccagttcaca gaaggttcc agtgtttatt cacaatgaga agcccatagc | 300 |
| agagtctctt gtgattgttg aatacattga tgagacatgg aagaacaacc ccatcttgcc | 360 |
| ttctgatcct taccaaagag ccttggctcg tttctggtcc aaattcattg atgacaaggt | 420 |
| tgtgggtgct gcatggaaat atatttatac tgttgatgag aaagagcgtg agaagaatgt | 480 |
| tgaagagtca tatgaggctc tgcagtttct tgagaatgca ctgaaggaca gaagttttt | 540 |
| tggaggagag gaaattgggt tggtagatat tgctgctgtc ttcatagcat tttggatccc | 600 |
| tataattcaa gaagtattgg gtttgaagtt attcacaagt gagaaatttc ctaagctcta | 660 |
| caaatggagc caagagttca tcaaccaccc tgttgtcaaa caagtccttc ctcctagaga | 720 |
| tcaactttt gccttctaca aagcctgcca tgaaagtctt tctgcttcaa atagactta | 780 |
| tttaaggata gttgtgtgaa ctactggtct ctcatttgtg agttattgca gtttgaattt | 840 |
| catgtcaatt tggttttata tgtaatttag taacctggga tatctcccat ggagaaaata | 900 |
| atccttggat cttgtttcca ttttggccat ttcagttaat aaagaaattc atttttcca | 960 |
| aaaaaaaaaa aaaaaaa | 977 |

<210> SEQ ID NO 41
<211> LENGTH: 1006
<212> TYPE: DNA
<213> ORGANISM: Glycine max

<400> SEQUENCE: 41

| | |
|---|---|
| atagtgctgc aatggcttca agtcaggagg aggtgaccct tttgggagct actggaagcc | 60 |
| catttgtgtg cagggttcat attgccctca agttgaaggg agttcaatac aaatatgtcg | 120 |
| aagaaaattt gaggaacaag agtgaactgc ttctcaaatc caacccagtt cacagaaagg | 180 |
| ttccagtgtt tattcacaat gagaagccca tagcagagtc tcttgtgatt gttgaataca | 240 |
| ttgatgagac atgaagaac aaccccatct tgccttctga tccttaccaa agagccttgg | 300 |
| ctcgtttctg gtccaaattc attgatgata aggttttgg tgctgcatgg aaatccgttt | 360 |
| tcacagctga tgagaaagag cgtgagaaga atgttgagga agcaattgag ctctgcagtt | 420 |
| tcttgagaat gagataaagg acaagaagtt ctttggagga gaggagattg ggttggtaga | 480 |
| tattgctgct gtctacatag cattttgggt ccctatggtt caagaaattg cagggttgga | 540 |
| gttattcaca agtgagaaat tccctaagct ccacaattgg agccaagaat ttttgaacca | 600 |
| tccaattgtc aaagaaagtc tgcccccctag agatcctgtt ttctcctttt tcaagggtct | 660 |
| ctatgaaagc cttttttggtt caaaatagat ttgatgatgt ggtgtgagac ttagtatttc | 720 |

```
taagaattat gtgtttgtta aaggcttcta tgaaagcctc actgcttcaa aatagattca      780
tgtatgtgag actcagaatc tctggggaaa attgtgtgtg gtgtggacta cttgttttgt      840
ttgtcattga gctatatcgc tgttaattag gattttgttt caaaatgatg cttataagtt      900
gtaatctagg atttctccct tgaaatcct aggttgttct tgacatttgc tatttcaaag       960
aataaatata tagcatcttt ctatttctca aaaaaaaaaa aaaaaa                    1006

<210> SEQ ID NO 42
<211> LENGTH: 885
<212> TYPE: DNA
<213> ORGANISM: Glycine max

<400> SEQUENCE: 42
ccatagcaat ggcagagcaa gacaaggtga tcctacacgg gatgtgggcc agcccttatg       60
ccaagagggt ggaattggcc cttaatttta agggcatacc ctatgagtat gttgaagaag      120
acttgagaaa taagagtgat tgcttctaa agtacaaccc tgttcacaag aaggttcctg       180
tacttgttca taatgaaaag gccattgctg aatccatggt gatccttgag tatattgatg      240
aaacatggaa agatggtcct aaactgcttc caagtgattc ttacaaacga gcccaagctc      300
gattctggtg tcatttcatc caggatcagt taatggagag cacttttcta gtagtcaaaa      360
ctgatggaga agcacaacaa aaggccattg accacgtgta tgagaaactg aaagtgctag      420
aagatggaat gaagacctat ctgggagaag gcaatgctat tatctctggt gttgaaaaca      480
actttggaat ccttgacatt gtgttttgtg ctttatatgg tgcctacaag gctcatgaag      540
aagttattgg cctcaagttc atagtgccag aaaagtttcc tgtgttgttt cttggttga      600 tggctattgc tgaggttgaa gctgtgaaaa ttgcaactcc tccacatgaa aaacagtgg      660 gaattcttca gttgttcagg ctgtctgcac tgaaatcttc ttctgccaca gaatgatata      720
tacttcaaca ctttaataga ctgtccatcg tttgcttctt ctgcgagtct ttagtgtatg      780
tatctttcaa taacaggatg agtaacacct gagtatgtaa agcgtgatga tatagagata      840
tacctctata tatcaaatac tcttctataa aaaaaaaaa aaaaa                       885

<210> SEQ ID NO 43
<211> LENGTH: 991
<212> TYPE: DNA
<213> ORGANISM: Artificial Sequence
<220> FEATURE:
<223> OTHER INFORMATION: Description of Artificial Sequence:
      SSM.PK0067.G5

<400> SEQUENCE: 43
ctcgtgccgt ttctataaag gccaaactca caaccacac cctaacaaat tcatcttatt        60
ttgcaacaca attcaatttt gagcacttac caacaccact tccaatggct tcatatcatg      120
aagaagaagt gaggctattg ggcaagtggg ccagcccatt tagcaacaga gtagaccttg      180
ctctcaagct caagggtgtt ccctacaaat actccgagga agatcttgct aacaagagtg      240
ctgatcttct caagtacaac cccgttcaca agaaggttcc ggttttggtc cacaatggga      300
acccattgcc cgagtcactc atcattgttg aatacataga tgagacgtgg aaaaataacc      360
cactattgcc tcaagaccca tatgaaagag ccttggctcg ttttggtct aagacccttag      420 atgacaagat cttgccagct atatggaatg cttgctggag tgacgagaat gggcgtgaga      480
aagcagtgga ggaagccttg gaagcattga aaatcctaca ggaaacactg aaagacaaga      540
aattctttgg aggagagagc ataggattgg tagatattgc tgccaatttc attgggtatt      600
```

-continued

```
gggttgccat attgcaagag attgcagggt tggagttgct caccattgag aaatttccca        660
agttatataa ttggagtcaa gactttatca accaccctgt gatcaaggag ggtctgcctc        720
ctagagatga attgtttgct ttcttcaaag cttctgctaa aaagtagaac cattttagag        780
gtaggattca taataagtta gtatgatttt gttgggaaac aattatcttg ttgtgagcaa        840
aggattgttc tgttttaaat ttaattgact gtgatttggt tgggtattgg ctattttaat        900
tttaactaaa aaaagtgttc agttttaaaa aaaaaaaaaa aaaaaaaaaa aaaaaaaaa        960 aaaaaaaaaa aaaaaaaaaa aaaaaaaaaa a                                       991
```